(12) United States Patent
Kawai et al.

(10) Patent No.: US 9,535,033 B2
(45) Date of Patent: Jan. 3, 2017

(54) SAMPLE ANALYSIS METHOD

(71) Applicant: Quantum Biosystems Inc., Tokyo (JP)

(72) Inventors: Tomoji Kawai, Osaka (JP); Takahito Ohshiro, Osaka (JP); Masateru Taniguchi, Osaka (JP)

(73) Assignee: QUANTUM BIOSYSTEMS INC., Tokyo (JP)

( * ) Notice: Subject to any disclaimer, the term of this patent is extended or adjusted under 35 U.S.C. 154(b) by 0 days.

(21) Appl. No.: 14/421,809

(22) PCT Filed: Aug. 2, 2013

(86) PCT No.: PCT/JP2013/071059
§ 371 (c)(1),
(2) Date: Feb. 13, 2015

(87) PCT Pub. No.: WO2014/027580
PCT Pub. Date: Feb. 20, 2014

(65) Prior Publication Data
US 2015/0219593 A1    Aug. 6, 2015

(30) Foreign Application Priority Data
Aug. 17, 2012   (JP) ................................. 2012-181104

(51) Int. Cl.
*G01N 27/403* (2006.01)
*G01N 27/453* (2006.01)
(Continued)

(52) U.S. Cl.
CPC ........ *G01N 27/447* (2013.01); *G01N 15/1031* (2013.01); *G01N 27/3275* (2013.01);
(Continued)

(58) Field of Classification Search
CPC ..................... G01N 27/4473; G01N 33/48721
See application file for complete search history.

(56) References Cited

U.S. PATENT DOCUMENTS 5,092,972 A    3/1992   Ghowsi
5,122,248 A    6/1992   Karger et al.
(Continued)

FOREIGN PATENT DOCUMENTS

CN    101920932 A    12/2010
JP    H 0774337 A     3/1995
(Continued)

OTHER PUBLICATIONS

Woolley et al, "Capillary Electrophoresis Chips with Integrated Electrochemical Detection," Anal. Chem. 1998, 70, 684-688.*
(Continued)

*Primary Examiner* — Alexander Noguerola
(74) *Attorney, Agent, or Firm* — Wilson Sonsini Goodrich & Rosati

(57) ABSTRACT

The analysis method allows analysis of samples with high sensitivity, irrespective of interelectrode distance. The method includes: a step of applying a voltage between a first electrode pair such that an electric field is formed in a direction intersecting a migration direction of a sample; a step of placing a solution, including an electrochemically active molecule that produces a redox reaction at the electrode pair, between the first electrode pair; a step of causing the sample to migrate; and a step of measuring an amount of change in current flow between the first electrode pair.

15 Claims, 18 Drawing Sheets

(51) Int. Cl.
  *G01N 27/447* (2006.01)
  *G01N 27/327* (2006.01)
  *G01N 33/487* (2006.01)
  *G01N 15/10* (2006.01)

(52) U.S. Cl.
  CPC ... *G01N 27/4473* (2013.01); *G01N 33/48721* (2013.01); *G01N 2015/1006* (2013.01)

(56) References Cited

U.S. PATENT DOCUMENTS

| | | | |
|---|---|---|---|
| 5,151,164 A | 9/1992 | Blanchard et al. | |
| 5,262,031 A | 11/1993 | Lux et al. | |
| 5,593,838 A | 1/1997 | Zanzucchi et al. | |
| 5,906,723 A * | 5/1999 | Mathies | G01N 27/4473 204/601 |
| 6,159,353 A * | 12/2000 | West | G01N 27/44791 204/601 |
| 6,491,805 B1 | 12/2002 | Gordon et al. | |
| 6,613,513 B1 | 9/2003 | Parce et al. | |
| 7,033,476 B2 | 4/2006 | Lee et al. | |
| 7,892,414 B1 | 2/2011 | Sumner | |
| 7,918,979 B2 | 4/2011 | Han et al. | |
| 8,333,934 B2 | 12/2012 | Cao et al. | |
| 9,194,838 B2 | 11/2015 | Taniguchi et al. | |
| 2001/0046681 A1 | 11/2001 | Senapathy | |
| 2003/0085719 A1 | 5/2003 | Yoon et al. | |
| 2003/0089606 A1 | 5/2003 | Parce et al. | |
| 2003/0141189 A1 | 7/2003 | Lee et al. | |
| 2004/0144658 A1 | 7/2004 | Flory | |
| 2005/0048513 A1 | 3/2005 | Harwit et al. | |
| 2005/0061669 A1 | 3/2005 | Woudenberg et al. | |
| 2005/0127035 A1 | 6/2005 | Ling | |
| 2005/0136419 A1 | 6/2005 | Lee | |
| 2005/0202444 A1 | 9/2005 | Zhu | |
| 2005/0202446 A1* | 9/2005 | Yang | G01N 33/48721 435/6.11 |
| 2005/0227239 A1 | 10/2005 | Joyce | |
| 2006/0057585 A1 | 3/2006 | McAllister | |
| 2006/0154400 A1 | 7/2006 | Choi et al. | |
| 2006/0210995 A1 | 9/2006 | Joyce | |
| 2007/0029911 A1 | 2/2007 | Hudspeth et al. | |
| 2007/0042366 A1 | 2/2007 | Ling | |
| 2008/0171316 A1 | 7/2008 | Golovchenko et al. | |
| 2009/0023146 A1 | 1/2009 | Harnack et al. | |
| 2009/0155917 A1 | 6/2009 | Umezawa et al. | |
| 2009/0215156 A1 | 8/2009 | Chung et al. | |
| 2009/0242429 A1 | 10/2009 | Sitdikov et al. | |
| 2009/0286936 A1 | 11/2009 | Ogata et al. | |
| 2010/0025249 A1 | 2/2010 | Polonsky et al. | |
| 2010/0066348 A1 | 3/2010 | Merz et al. | |
| 2010/0084276 A1 | 4/2010 | Lindsay | |
| 2010/0184062 A1 | 7/2010 | Steinmuller-Nethl et al. | |
| 2010/0188109 A1 | 7/2010 | Edel et al. | |
| 2010/0243449 A1 | 9/2010 | Oliver | |
| 2010/0292101 A1 | 11/2010 | So | |
| 2010/0331194 A1 | 12/2010 | Turner et al. | |
| 2011/0056845 A1 | 3/2011 | Stellacci et al. | |
| 2011/0236984 A1 | 9/2011 | Sun et al. | |
| 2011/0250464 A1 | 10/2011 | Wilson et al. | |
| 2011/0287956 A1 | 11/2011 | Iqbal et al. | |
| 2012/0041727 A1 | 2/2012 | Mishra et al. | |
| 2012/0097539 A1 | 4/2012 | Qian et al. | |
| 2012/0132886 A1 | 5/2012 | Peng et al. | |
| 2012/0193237 A1 | 8/2012 | Afzali-Ardakani et al. | |
| 2012/0199485 A1 | 8/2012 | Sauer et al. | |
| 2012/0254715 A1 | 10/2012 | Schwartz | |
| 2012/0298511 A1 | 11/2012 | Yamamoto | |
| 2012/0322055 A1 | 12/2012 | Royyuru | |
| 2013/0001082 A1 | 1/2013 | Afzali-Ardakani et al. | |
| 2013/0092547 A1 | 4/2013 | Li et al. | |
| 2013/0186758 A1 | 7/2013 | Saha et al. | |
| 2014/0001055 A1 | 1/2014 | Elibol et al. | |
| 2014/0031995 A1 | 1/2014 | Kawai et al. | |
| 2014/0055150 A1 | 2/2014 | Kawai et al. | |
| 2014/0183040 A1 | 7/2014 | Kawai et al. | |
| 2014/0300339 A1 | 10/2014 | Taniguchi et al. | |
| 2014/0374695 A1 | 12/2014 | Astier et al. | |
| 2016/0049327 A1 | 2/2016 | Singh et al. | |
| 2016/0138101 A1 | 5/2016 | Taniguchi et al. | |
| 2016/0245789 A1 | 8/2016 | Ikeda et al. | |
| 2016/0245790 A1 | 8/2016 | Kawai et al. | |

FOREIGN PATENT DOCUMENTS

| | | |
|---|---|---|
| JP | 2003/090815 A | 3/2003 |
| JP | 2003/332555 A | 11/2003 |
| JP | 2003/533676 A | 11/2003 |
| JP | 2004/233356 A | 8/2004 |
| JP | 2005/257687 A | 9/2005 |
| JP | 2006/078491 A | 3/2006 |
| JP | 2006/526777 A | 11/2006 |
| JP | 2007/272212 A | 10/2007 |
| JP | 2008/032529 A | 2/2008 |
| JP | 4128573 B2 | 7/2008 |
| JP | 2008/186975 A | 8/2008 |
| JP | 2008/536124 A | 9/2008 |
| JP | 2009/527817 A | 7/2009 |
| JP | 2009/272432 A | 11/2009 |
| JP | 2010/513853 A | 4/2010 |
| JP | 2010/227735 A | 10/2010 |
| JP | 2011/500025 A | 1/2011 |
| JP | 2011/054631 A | 3/2011 |
| JP | 2011/516050 A | 5/2011 |
| JP | 2011/163934 A | 8/2011 |
| JP | 2011/211905 A | 10/2011 |
| JP | 2012/110258 A | 6/2012 |
| JP | 2013/036865 A | 2/2013 |
| JP | 2014/074599 A | 4/2014 |
| JP | 2015/059824 A | 3/2015 |
| JP | 2015/077652 A | 4/2015 |
| WO | WO 01/13088 A1 | 2/2001 |
| WO | WO 01/81896 A1 | 11/2001 |
| WO | WO 01/81908 A1 | 11/2001 |
| WO | WO 03/018484 A1 | 3/2003 |
| WO | WO 03/106693 A2 | 12/2003 |
| WO | WO 2007/013370 A1 | 2/2007 |
| WO | WO 2008/079169 A2 | 7/2008 |
| WO | WO 2009/045472 A1 | 4/2009 |
| WO | WO 2009/093019 A2 | 7/2009 |
| WO | WO 2009/120642 A1 | 10/2009 |
| WO | WO 2009/149362 A2 | 12/2009 |
| WO | WO 2010/116595 A1 | 10/2010 |
| WO | WO 2011/082419 A1 | 7/2011 |
| WO | WO 2011/097171 A1 | 8/2011 |
| WO | WO 2011/108540 A1 | 9/2011 |
| WO | WO 2012/164679 A1 | 12/2012 |
| WO | WO 2012/170560 A2 | 12/2012 |
| WO | WO 2013/076943 A1 | 5/2013 |
| WO | WO 2013/100949 A1 | 7/2013 |
| WO | WO 2013/116509 A1 | 8/2013 |
| WO | WO 2013/147208 A1 | 10/2013 |

OTHER PUBLICATIONS

Lee et al., "Surface Charge Study on Pollen with a Simple Microelectrophoresis Instrumentation Setup," 2010 IEEE EMBS Conference on Biomedical Engineering & Sciences (IECBES 010), Kuala Lumpur, Malaysia, Nov. 30-Oct. 2, 2010, pp. 364-368.*

Smith et al., "Electrophoretic distributions of human peripheral mononuclear white blood cells from normal subjects and from patients with acute lymphocytic leukemia," Proc. Natl. Acad. Sci. USA vol. 73, No. 7, pp. 2388-2391, Jul. 1976 Biophysics.*

Xiaogan et al., Nanogap Detector inside Nanoflidc Channel for Fast Real-Time Label-Free DNA Analysis, Nano Letters, 2008, vol. 8, No. 5, pp. 1472-1476.*

Carter et al., "Votammetric Studies of the Interaction of Metal Chelates with DNA 2. Tris-Chelated Complexes of Cobalt(III) and Iron (II) with 1,10-Phenanthroline and 2,2'-Bipyridine," J. Am. Chem. Soc. 1989, 111, 8901-8911.*

EPO computer-generated English language translation of CN101920932. Downloaded Sep. 7, 2016.*

(56) References Cited

OTHER PUBLICATIONS

Bagci, et al. Recognizing nucelotides by cross-tunneling currents for DNA sequencing. Physical Review E, vol. 84, Issue No. 1, Article No. 011917 (internal pp. 1-4) (2011).

Branton, et al. The potential and challenges of nanopore sequencing. Nature Biotechnology, vol. 26, No. 10, Oct. 2008, pp. 1146-1153.

Brown, et al. Nucleotide—Surface Interactions in DNA-Modified Au—Nanoparticle Conjugates: Sequence Effects on Reactivity and Hybridization. J. Phys. Chem. C, 2008, 112 (20), pp. 7517-7521.

Chang, et al. Tunnelling readout of hydrogen-bonding-based recognition. Nature Nantechnology, vol. 4, May 2009, pp. 297-301.

Clarke, et al. Continuous base identification for single-molecule nanopore DNA sequencing. Nat Nanotechnol. Apr. 2009;4(4):265-70. doi: 10.1038/nnano.2009.12. Epub Feb. 22, 2009.

Dekker, et al. Solid-state nanopores. Nature Nanotechnology, vol. 2, Apr. 2007, pp. 209-215.

Fischbein, et al. Sub-10 nm Device Fabrication in a Transmission Electron Microscope. American Chemical Society, Nano Letters, 2007, vol. 7, No. 5, pp. 1329-1337.

Fologea, et al. Detecting Single Stranded DNA with a Solid State Nanopore. American Chemical Society, Nano Letters, 2005, vol. 5, No. 10, pp. 1905-1909.

He, et al. Identification of DNA Basepairing via Tunnel-Current Decay. American Chemical Society, Nano Letters, 2007, vol. 7, No. 12, pp. 3854-3858.

International search report and written opinion dated Oct. 29, 2013 for PCT Application No. JP2013/071059.

International search report and written opinion dated Dec. 19, 2014 for PCT Application No. US2014/056173.

Keyser, et al. Direct force measurements on DNA in a solid-state nanopore. Nature Physics, vol. 2, Jul. 2006, pp. 473-477.

Lagerqvist, et al. "Fast DNA Sequencing via Transverse Electronic Transport", American Chemical Society, Nano Letters, 2006, vol. 6, No. 4, pp. 779-782.

Lagerqvist, et al. Influence of the Environment and Probes on Rapid DNA Sequencing via Transverse Electronic Transport. Biophysical Journel, vol. 93, Oct. 2007, pp. 23842390.

Li, et al. Ion-beam sculpting at nanometer length scales. Nature, vol. 412, Jul. 2001, pp. 166-169.

Liang, et al. Nanogap Detector Inside nanofluidic Channel for Fast Real-Time Label-Free DNA Analysis. American Chemical Society, Nano Letters 2008, vol. 8, No. 5, pp. 1472-1476.

Maleki, et al. A nanofluidic channel with embedded transverse nanoelectrodes. Nanotechnology, 20, (2009) 105302, pp. 1-6.

Oshiro, et al. Detection of post-translational modifications in single peptides using electron tunnelling currents. Nature Nanotechnology, vol. 9, pp. 835-840 (e-pub. Sep. 14, 2014).

Oshiro, et al. Single-molecule electrical random resequencing of DNA and RNA. Scientific Reports, vol. 2, Article No. 501 (internal pp. 1-7) (e-pub. Jul. 10, 2012) See abstract: p. 2; figures 1-4; and tables 1-3.

Pedone, et al. Data Analysis of Translocation Events in Nanopore Experiments. American Chemical Society, Anal. Chem. 2009, 81, pp. 9689-9694.

Peng, et al. Reverse DNA translocation through a solid-state nanopore by magnetic tweezers. Nanotechnology. May 6, 2009;20(18):185101. doi: 10.1088/0957-4484/20/18/185101. Epub Apr. 14, 2009.

Ruitenbeek, et al. Adjustable nanofabricated atomic size contacts. Rev. Sci. Instrum. 67, 108 (1996).

Simmons, et al. Generalized Formula for the Electric tunnele Effect between Similar Electrodes Separated by a Thin Insulating Film. J. Appl. Phys. 34, 1793 (1963).

Stijin Van Dorp, et al. Origin of the electrophoretic force on DNA in solid-state nanopores. Nature Physics, vol. 5, May 2009, pp. 347-351.

Stoddart, et al. Single-nucleotide discrimination in immobolized DNA oligonucleotides with a biological nanopore. PNAS, May 12, 2009, vol. 106, No. 19, pp. 7702-7707.

Storm, et al. Fabrication of solid-state nanopores with single-nanometere precision. Nature Materials, Vol2, Aug. 2003, pp. 537-540.

Taniguchi, et al. Development of Single-Molecule Bio-Nanodevies for Medical Applications. The Imaging Society of Japan, Feb. 10, 2013, vol. 52, No. 1, pp. 51-60.

Trepagnier, et al. Controlling DNA Capture and Progagation through Artificial Nanopores. American Chemical Society, Nano Letters, 2007, vol. 7, No. 9, pp. 2824-2830.

Tsutsui, et al. Fabrication of 0.5 nm electrode gaps using self-breaking technique. Applied Physics Letters 93, 163115 (2008); DOI: 10.1063/1.3006063.

Tsutsui, et al. Formation and self-breaking mechanism of stable atom-sized junctions. Nano Lett. Jan. 2008;8(1):345-9. Epub Dec. 21, 2007.

Tsutsui, et al. Identifying single nucleotides by tunnelling current. Nature Nanotechnology, Letters, Published Online. Mar. 21, 2010; DOI: 10.1038/NNANO.2010.42, pp. 1-5.

Tsutsui, et al. Transverse Field Effects on DNA-Sized Particle Dynamics. American Chemical Society, Nano Letters, 2009, vol. 9, No. 4, pp. 1659-1662.

Wang, et al. Mechanism of electron conduction in self-assembled alkanethiol monolayer devices. Phys. Rev. B 68, 035416—Published Jul. 17, 2003.

Yen, et al. Gate effects on DNA translocation through silicon dioxide nanopore. Rev Sci Instrum. Mar. 2012;83(3):034301. doi: 10.1063/1.3692746.

Zwolak, et al. Colloquium: Physical approaches to DNA sequencing and detection. Reviews of Modern Physics, vol. 80, Jan.-Mar. 2008, pp. 141-165.

Zwolak, et al. Electronic Signature of DNA Nucleotides via Transverse Transport. American Chemical Society, Nano Letters, 2005, vol. 5, No. 3, pp. 421-424.

U.S. Appl. No. 14/883,494, filed Oct. 14, 2015, Taniguchi et al.

Troisi, et al. Molecular signatures in the transport properties of molecular wire junctions: what makes a junction "molecular" ? Small. Feb. 2006;2(2):172-81.

Notice of allowance dated Oct. 8, 2015 for U.S. Appl. No. 13/992,328.

U.S. Appl. No. 14/687,856, filed Apr. 15, 2015, Ikeda.

International Preliminary Report on Patentability dated Jun. 25, 2013 for PCT Application No. JP2013/059645.

International search report and written opinion dated Jan. 26, 2015 for PCT Application No. US2014/060742.

International search report dated Feb. 17, 2015 for PCT Application No. IB2014/002143.

International search report dated Jun. 25, 2013 for PCT Application No. JP2013/059645.

Office action dated Apr. 17, 2015 for U.S. Appl. No. 13/992,328.

Taniguchi, et al. Denryu de Ichi Enki Bunshi o Shikibetsu suru. Chemistry, 2011, vol. 66, No. 8, pp. 42-46.

Taniguchi, M. Ichibunshi Kaiseki Gijutsu ni yoru Jijisedai DNA Sequencer no Kaihatsu. Dai 69 Kai Hyomen Kagaku Kenkyukai Yoshishu. Mar. 9, 2011, pp. 23-26.

Zhou, et al. Microfabrication of a mechanically controllable break junction in silicon. Appl. Phys. Lett. 67, 1160 (1995).

Furuhashi, et al. High speed DNA denaturation using microheating devices. Appl. Phys. Lett., Jul. 11, 2013 103, pp. 023112.

International search report dated Feb. 24, 2015 for PCT Application No. IB2014/002128.

Kaji, et al. Separation of long DNA molecules by quartz nanopillar chips under a direct current electric field. Anal. Chem., Jan. 1, 2004 76(1): pp. 15-22.

Nadasan, et al. Design and fabrication of the microchannels for microfluidics applications. U.P.B. Sci. Bull., Series C, 2009, 71(4): pp. 125-134.

Notice of allowance dated Jul. 21, 2016 for U.S. Appl. No. 13/975,610.

Office action dated Aug. 1, 2016 for U.S. Appl. No. 14/112,189.

Qiu, et al. Detecting ssDNA at single-nucleotide resolution by sub-2-nanometer pore in monatomic graphene: A molecular dynamics study. Applied Physics Letters 100.8 (2012): 083106. 4 pages.

(56) References Cited

OTHER PUBLICATIONS

Zhao, et al. Single-strand DNA molecule translocation through nanoelectrode gaps. Nanotechnology. Oct. 24, 2007;18(42):424018. doi: 10.1088/0957-4484/18/42/424018. Epub Sep. 19, 2007 7 pages.
U.S. Appl. No. 15/217,821, filed Jul. 22, 2016, Kawai et al.
Gierhart, et al. Nanopore with transverse nanoelectrodes for electrical characterization and sequencing of DNA. Sens Actuators B Chem. Jun. 16, 2008;132(2):593-600.
International search report and written opinion dated May 19, 2015 for PCT/JP2015/054796.
International search report and written opinion dated Jun. 24, 2015 for PCT/JP2015/052601.
International search report and written opinion dated Aug. 11, 2015 for PCT/JP2015/063403.
International search report and written opinion dated Aug. 18, 2015 for PCT/JP2015/063964.
International search report and written opinion dated Aug. 18, 2015 for PCT/JP2015/063965.
International search report and written opinion dated Aug. 18, 2015 for PCT/JP2015/063963.
Ivanov, et al. DNA tunneling detector embedded in a nanopore. Nano Lett. Jan. 12, 2011;11(1):279-85. doi: 10.1021/nl103873a. Epub Dec. 6, 2010.
Lesser-Rojas, et al. Tandem array of nanoelectronic readers embedded coplanar to a fluidic nanochannel for correlated single biopolymer analysis. Biomicrofluidics. Jan. 10, 2014;8(1):016501. doi: 10.1063/1.4861435. eCollection 2014. With Supplementary Materials.
Ohshiro, et al. Single-molecule electrical random resequencing of DNA and RNA. Scientific Reports 2, Article No. 501 (Jul. 10, 2012) doi:10.1038/srep00501.
Venkatesan, et al. Nanopore sensors for nucleic acid analysis. Nat Nanotechnol. Sep. 18, 2011;6(10):615-24. doi: 10.1038/nnano.2011.129.
U.S. Appl. No. 15/048,810, filed Feb. 19, 2016, Ikeda et al.
U.S. Appl. No. 15/048,889, filed Feb. 19, 2016, Kawai et al.
U.S. Appl. No. 15/061,871, filed Mar. 4, 2016, Kawai et al.
U.S. Appl. No. 15/098,147, filed Apr. 13, 2016, Ikeda et al.
He, et al. Controlling DNA translocation through gate modulation of nanopore wall surface charges. ACS Nano. Jul. 26, 2011;5(7):5509-18. doi: 10.1021/nn201883b. Epub Jun. 17, 2011.
Nam, et al. Ionic field effect transistors with sub-10 nm multiple nanopores. Nano Lett. May 2009;9(5):2044-8. doi: 10.1021/n1900309s.
Office action dated Feb. 5, 2016 for U.S. Appl. No. 14/112,189.
Office action dated Feb. 19, 2016 for U.S. Appl. No. 13/975,610.
Cheng, et al. Development of an electrochemical membrane-based nanobiosensor for ultrasensitive detection of dengue virus. Anal Chim Acta. May 6, 2012;725:74-80. doi: 10.1016/j.aca.2012.03.017. Epub Mar. 17, 2012.
European search report and opinion dated Apr. 8, 2016 for EP Application No. 13879507.5.
Gonzalez, et al. Mass transport effect of mesoscopic domains in the amperometric response of an electroactive species: Modeling for its applications in biomolecule detection. Sensors and Actuators B: Chemical 144.2 (2010): 349-353.
He, et al. Gate manipulation of DNA capture into nanopores. ACS Nano. Oct. 25, 2011;5(10):8391-7. doi: 10.1021/nn203186c. Epub Sep. 26, 2011.
He, et al. Thermophoretic manipulation of DNA translocation through nanopores. ACS Nano. Jan. 22, 2013;7(1):538-46. doi: 10.1021/nn304914j. Epub Dec. 10, 2012.
Office action dated Jun. 23, 2016 for U.S. Appl. No. 14/111,352.
Tsutsui, et al. Transverse electric field dragging of DNA in a nanochannel. Sci Rep. 2012;2:394. doi: 10.1038/srep00394. Epub May 3, 2012.
Huang, et al. Identifying single bases in a DNA oligomer with electron tunnelling. Nat Nanotechnol. Dec. 2010;5(12):868-73. doi: 10.1038/nnano.2010.213. Epub Nov. 14, 2010.
Notice of allowance dated Jul. 17, 2015 for U.S. Appl. No. 13/992,328.
Office action dated Sep. 1, 2015 for U.S. Appl. No. 14/112,189.
Office action dated Aug. 26, 2016 for U.S. Appl. No. 14/687,856.
Office action dated Sep. 9, 2016 for U.S. Appl. No. 15/061,871.
Office action dated Oct. 6, 2016 for U.S. Appl. No. 14/883,494.

* cited by examiner

SAMPLE ANALYSIS METHOD

CROSS-REFERENCE

This application is a National Stage Entry of International Patent Application No. PCT/JP2013/071059, filed Aug. 2, 2013, which claims priority to Japanese Patent Application No. 2012-181104, filed Aug. 17, 2012, each of which is incorporated herein by reference in its entirety.

TECHNICAL FIELD

The present invention relates to a sample analysis method.

BACKGROUND ART

Conventionally, methods for analyzing diverse types of samples, and determining various characteristics of such samples using current measurement techniques, have been under development.

For example, techniques for analysis of DNA nucleotide sequences are used not only in scientific research, but also in numerous other fields, such as in medical treatment, drug development, and criminal investigation, with increasing interest in the development of such techniques. Therefore, previously, techniques are being developed for analyzing DNA nucleotide sequences by measuring electrical current.

For example, techniques are being developed for performing sequencing employing a single molecule of DNA, by detecting short-lived interruptions in ionic current that occur as a single-stranded DNA passes through nanopores formed by proteins embedded in cyclodextrin (see, for example, Non-patent Documents 1 and 2).

However, these techniques have many issues, such as: (1) pore size cannot be changed; and (2) such systems are unstable since the nanopores are formed by proteins. The development of techniques different from such techniques has therefore been desired.

Under these circumstances, a sequencing theory has been proposed based on transverse electron transport. This theory is based on principles regarding detection of a characteristic transverse conductivity of each nucleotide as nucleotides pass through the interior of a nanoscale space between a pair of electrodes. This conductivity relates to the different HOMO-LUMO gap of each nucleotide.

Specifically, when single-stranded DNA passes through a nanopore interior, a tunneling current is produced between an electrode pair, the electrode pair having a nanoscale interelectrode distance and provided at the edges of the nanopore, through each nucleotide constituting the single-stranded DNA. Then, each of the nucleotides constituting the single-stranded DNA can be directly identified, without labeling, by measuring the current value of the tunneling current (see, for example, Patent Document 1).

Related Patent Documents

Patent Document 1: WO2011/108540A1 (laid-open on Sep. 9, 2011)

Non-patent Documents

Non-patent Document 1: J Clarke, H C Wu, L Jayasinghe, A Patel, S Reid, H Bayley, Nat. Nanotechnol. 4, 265 (2009)
Non-patent Document 2: D Stoddart, A J Heron, E Mikhailova, G Maglia, H Bayley, Proc. Natl. Acad. Sci. USA 106, 7702 (2009)

SUMMARY OF INVENTION

Technical Problem

However, in the techniques described, as the distance between the electrodes increases, the value of the detectable current becomes extremely small, which is therefore a problem since samples cannot be analyzed with high sensitivity.

Specifically, if the distance between the electrodes is 2 nm or greater, the value of the tunneling current flowing between the electrodes becomes extremely small. Consequently, techniques that analyze various samples based on tunneling current have problems in that samples cannot be analyzed with high sensitivity if the distance between the electrodes is 2 nm or greater.

That is, techniques that analyze various samples based on tunneling current are problematic in that the analytical ability thereof varies greatly according to the distance between the electrodes (in other words, the size of the sample).

In consideration of the conventional issues above, an object of the invention is to provide a novel analytical method in which samples may be analyzed with high sensitivity, regardless of the distance between the electrodes.

Solution to Problem

In order to overcome these problems, the sample analysis method of the invention includes: a first step of applying a voltage between a first electrode pair, which is formed so as to sandwich a migration pathway of a sample such that an electric field is formed in a direction intersecting the migration direction of the sample; a second step of causing a first current, which arises from a redox reaction, to flow to the first electrode pair by placing, within the migration pathway interposed between the first electrode pair, a solution including an electrochemically active molecule that produces the redox reaction at the first electrode pair; a third step of causing the sample to migrate along the migration pathway interposed between the first electrode pair; and a fourth step of measuring an amount of change in the first current produced by migration of the sample.

According to this configuration, the solution containing the electrochemically active molecule that produces the redox reaction at the first electrode pair is placed within the migration pathway interposed between the first electrode pair in a state in which a voltage is applied across the first electrode pair. The electrochemically active molecule thereby causes a redox reaction at the first electrode pair, and the first current arising from the redox reaction flows to the first electrode pair. That is, in a state in which no sample is present, the first current arising from the redox reaction continues to flow to the first electrode pair, and the current forms a baseline of the first current.

Moreover, gas generation at the first electrode pair can be suppressed since, at this time, the electrochemically active molecule preferentially causes the redox reaction at the first electrode pair. If gas were generated at the first electrode pair, the redox reaction of the electrochemically active molecule would be hindered by the gas, and as a result, the first current would be an unstable current with a fluctuating value. For example, the more the surfaces of the first electrode pair are covered by gas, the lower the value of the first current, and the value of the first current would immediately increase when gas departs from the surfaces of the first electrode pair. The first current would become an unstable current with a fluctuating value due to repeat of this phenomenon. However, the described configuration suppresses generation of gas, and therefore enables the first current to be stabilized.

The sample is then caused to migrate along the migration pathway interposed between the first electrode pair. In other words, the sample is introduced into the space between the first electrode pair. When this occurs, a change is produced in the number of electrochemically active molecules present in the migration pathway interposed between the first electrode pair, according to the size (volume) of the sample, the type of charge held by the sample, and the charge quantity of the sample. The number of electrochemically active molecules present within the migration pathway is sometimes decreased and is sometimes increased.

When a change is produced in the number of electrochemically active molecules present within the migration pathway interposed between the first electrode pair, a change is produced in the number of electrochemically active molecules, giving rise to the redox reaction at the first electrode pair. That is, a change in the value of the first current is produced.

The amount of change in the value of the first current is correlated with various characteristics of the sample (for example, the volume, the type of charge, and the charge quantity). It is clearly possible to detect the presence of the sample, and it is possible to analyze various characteristics of the sample (for example, the volume, the type of charge, and the charge quantity), by measuring the amount of change in the first current.

The sample analysis method of the invention preferably includes a fifth step of calculating the volume of the sample from the measured amount of change in the first current, based on a correlation between the volume of a reference sample and an amount of change in the first current.

In this configuration, the correlation between the volume of the reference sample and the amount of change in the first current (for example, a function) is determined in advance using reference samples of known volumes. Thus, by measuring the amount of change in the first current for a sample of unknown volume, the volume of the sample of unknown volume can be estimated from the measured value and the correlation (in other words, by substituting the amount of change in the first current for the sample of unknown volume into the function).

The correlation is not limited to a direct correlation between the volume of the reference sample and the amount of change in the first current, and a correlation may be found that employs an amount of change in a physical quantity according to the first current. The physical quantity according to the first current may be, for example, a current value, a conductance, a resistance value, or the like. Moreover, a logarithm of these values, values obtained by normalizing these values, or the like, may be employed.

The sample analysis method of the invention preferably includes a sixth step of calculating the charge quantity of the sample from the amount of change in the first current, based on the correlation between the charge quantity of the reference sample and the amount of change in the first current.

In this configuration, the correlation between the charge quantity of the reference sample and the amount of change in the first current (for example, a function) is found in advance using reference samples having known charge quantity. By measuring the amount of change in the first current for a sample of unknown charge quantity, the charge quantity of the sample of unknown charge quantity can be estimated from the measured value and the correlation (in other words, by substituting the amount of change in the first current for the sample of unknown charge quantity into the function).

The correlation is not limited to a direct correlation between the charge quantity of the reference sample and the amount of change in the first current, and a correlation may be found that employs an amount of change in a physical quantity according to the first current. The physical quantity according to the first current may be, for example, a current value, conductance, a resistance value or the like. Moreover, a logarithm of these values, values obtained by normalizing these values, or the like, may be employed.

In the sample analysis method of the invention, it is preferable that: the first step further include applying a voltage between a second electrode pair, which is formed so as to sandwich a migration pathway of the sample such that an electric field is formed in a direction substantially parallel to the migration direction of the sample; the second step further includes causing a second current, which arises from ion migration along the migration direction of the sample in the migration pathway interposed between the first electrode pair, to flow to the second electrode pair by placing, within the migration pathway interposed between the first electrode pair, the solution including the electrochemically active molecule that produces the redox reaction at the first electrode pair; and the fourth step further includes measuring an amount of change in the second current produced by the migration of the sample.

In this configuration, the solution containing the electrochemically active molecule that produces the redox reaction at the first electrode pair is placed within the migration pathway interposed between the first electrode pair, in a state in which a voltage is applied between the second electrode pair. This enables the second current arising from ions migrating along the migration direction through the migration pathway interposed between the first electrode pair to be caused to flow to the second electrode pair. The current then forms a baseline of the second current.

The sample is then caused to migrate along the migration pathway interposed between the first electrode pair. In other words, the sample is introduced into the space between the first electrode pair. When this occurs, a change according to the size (volume) of the sample is produced in the number of ions migrating along the migration direction through the migration pathway interposed between the first electrode pair. Specifically, the larger the sample, the narrower the space through which ions can migrate and the lower the number of ions migrating, and as a result, the value of the second current decreases. It is obviously possible to detect the presence of the sample, and it is possible to analyze the size (volume) of the sample, by measuring the amount of change in the second current.

The sample analysis method of the invention preferably includes a seventh step of calculating the volume of the sample from the measured amount of change in the second current, based on a correlation between the volume of a reference sample and an amount of change in the second current.

In this configuration, the correlation between the volume of the reference sample and the amount of change in the second current (for example, a function) is found in advance using reference samples having a known volume. By measuring the amount of change in the second current of a sample of unknown volume, the volume of the sample of unknown volume can be estimated from the measured value and the correlation (in other words, by substituting the amount of change in the second current for the sample of unknown volume into the function).

The correlation is not limited to a direct correlation between the volume of the reference sample and the amount of change in the second current, and a correlation may be found that employs an amount of change in a physical quantity according to the first current. The physical quantity according to the second current may be, for example, a current value, conductance, a resistance value, or the like. Moreover, a logarithm of these values, values obtained by normalizing these values, or the like, may be employed.

In the sample analysis method of the invention, the electrochemically active molecule is preferably a metal complex, an organometallic complex, or an organic molecule.

This configuration enables implementation of the analysis method of the invention at low cost.

In the sample analysis method of the invention, the electrochemically active molecule is preferably a potassium hexacyanoferrate complex, a hexamine ruthenium complex chloride, or hydroxyferrocene.

In this configuration, a metal complex with a charge is formed when dissolved in the solution, enabling information related to the volume of the sample, information related to the type of charge of the sample, and information related to the charge quantity of the sample, to be obtained with better precision.

In the sample analysis method of the invention, the electrochemically active molecule preferably causes the redox reaction when a voltage of from −1V to 1V is applied.

This configuration enables a baseline with a large value for the first current to be obtained, and enables the first current to be stabilized. As a result, the sample can be analyzed with better sensitivity since the amount of change in the first current produced by migration of the sample can be increased.

In the sample analysis method of the invention, the distance between the anode and the cathode of the first electrode pair may be 2 nm or greater.

This configuration enables sample analysis with excellent sensitivity even with interelectrode distances that are problematic for tunneling current measurements.

In the sample analysis method of the invention, it is preferable that the first electrode pair be gold electrodes or platinum electrodes, the second electrode pair be silver/silver chloride electrodes, and a chloride ion be contained in the solution containing the electrochemically active molecule that produces the redox reaction at the first electrode pair.

This configuration enables preferential production of the redox reaction of the electrochemically active molecule at the first electrode pair. Consequently, this configuration enables more effective flow of the first current arising from the redox reaction at the first electrode pair, and for the second electrode pair, enables more effective flow of the second current arising from migration of the ions (the chloride ions) along the migration direction via the migration pathway interposed between the first electrode pair.

Advantageous Effects

The invention exhibits an advantageous effect of enabling sample analysis with high sensitivity regardless of interelectrode distance. Specifically, a solution including an electrochemically active molecule that produces a redox reaction at a first electrode pair is placed in a sample migration pathway interposed between the first electrode pair, and the sample is caused to migrate along the migration pathway. Accordingly, it is possible to measure an amount of change in a first current that has a correlation with various characteristics of the sample, enabling sample analysis with high sensitivity regardless of interelectrode distance.

The invention exhibits the advantageous effect of enabling amplification of a signal. Specifically, since a first current arising from the redox reaction flows to the first electrode pair in advance in the invention, the first current (in other words, the baseline of the first current) can be increased according to the type and the concentration of the electrochemically active molecule. Since the signal measured in the invention is the amount of change in the first current, the measured signal can be amplified by setting the first current at a high level.

The invention exhibits the advantageous effect of enabling the signal to be stabilized. Specifically, the first current arising from the redox reaction flows to the first electrode pair in advance in the invention, enabling the first current (in other words, the baseline of the first current) flowing to the first electrode pair to be stabilized. Since the signal measured in the invention is the amount of change in the first current, stabilizing the first current enables the measured signal to be stabilized.

Specifically, when no electrochemically active molecule is employed, the first current cannot be stabilized since the current flowing at the first electrode pair is random. More specifically, gas is produced at the first electrode pair if no electrochemically active molecule is employed, and the first current cannot be stabilized since the gas hinders the reaction (the redox reaction) produced at the first electrode pair.

The invention enables information related to the volume of the sample, information related to the type of charge of the sample, and information related to the charge quantity of the sample (for example, a surface charge quantity) to be obtained.

The invention enables tailored detection of samples by selecting the type of electrochemically active molecule.

The invention enables the mechanical strength and stability of the analytical device to be increased since biological molecules do not need to be employed as a material for forming the analytical device (for example, proteins for forming holes). As a result, it is possible to perform sample analysis with excellent precision even under harsh conditions (for example, under temperature conditions in which proteins denature, in the presence of organic solvents, and the like).

In conventional technology, it is necessary to dissolve a sample using solutions with a high salt concentration, or a solution with a high pH, in order to detect current flowing between the interelectrode gap with high sensitivity. Consequently, in conventional technology, when the sample is a cell or a virus, there is a risk of the cell or virus clumping or dying, and when the sample is a protein, there is a risk of the protein being inactivated. However, solutions with a high salt concentration and solutions with a high pH are unnecessary in the invention, enabling analysis of biological samples such as cells, viruses, and proteins under physiological conditions (for example, in an aqueous solution with a pH controlled to be from pH 6 to pH 8 by a buffer).

In the invention, fixing the sample to a substrate or the like is unnecessary, and it is possible to perform sequential analysis while samples are caused to migrate, enabling a remarkable increase in analytical performance (for example in analytical speed).

Since the invention enables the interelectrode distance to be set to a desired distance, analysis with excellent precision is possible not only for small samples, but also for large samples.

DESCRIPTION OF EMBODIMENTS

Explanation follows regarding an embodiment of the invention; however, the invention is not limited thereto. The invention may be modified within the scope of the claims, and the technical scope of the invention includes embodiments and examples obtainable by appropriate combination of the different technical means described for each of the embodiments and examples.

1. Principles of the Present Embodiment

First, explanation follows regarding the principles of the present embodiment, with reference to FIG. 1A to FIG. 5B.

Figure 1A:
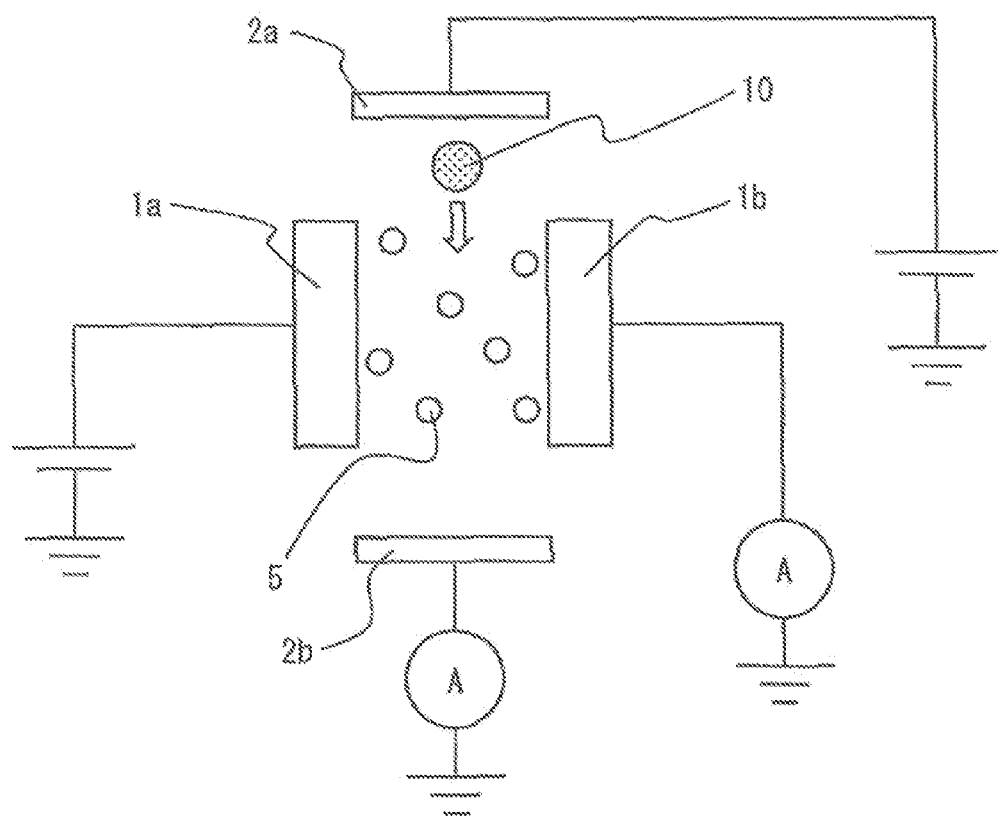
FIG. 1A is a diagram showing an analysis method of an embodiment of the invention.

As illustrated in FIG. 1A, in the present embodiment, a voltage is applied such that an electric field is formed in a direction intersecting a migration direction of a sample 10 (indicated by the arrow in FIG. 1), between a first electrode pair (an electrode 1a and an electrode 1b) formed so as to sandwich a migration pathway of a sample 10.

Moreover, in the present embodiment, within the migration pathway interposed between the first electrode pair (the electrode 1a and the electrode 1b), a first current arising from a redox reaction flows to the first electrode pair due to placing an electrolytic fluid including an electrochemically active molecule 5 that produces the redox reaction between the first electrode pair. That is, in the present embodiment, a baseline for the first current (see FIG. 1B) is formed by the first current that arises from the redox reaction in a state in which no sample is present. The magnitude of the first current depends on the type of electrochemically active molecule 5, and the concentration thereof (in other words, the number of electrochemically active molecules 5 present between the electrode 1a and the electrode 1b).

Figure 1B:
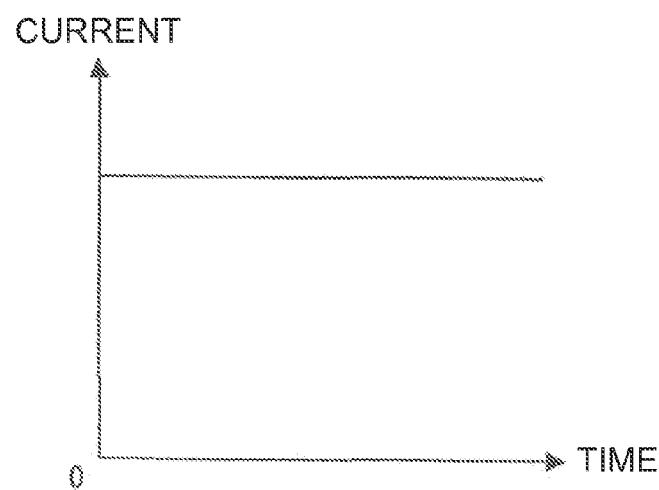
FIG. 1B is a diagram showing an analysis method of an embodiment of the invention.

In modes that do not employ the electrochemically active molecule 5, current flows at random between the first electrode pair, and a stable baseline current like that illustrated in FIG. 1B is not able to form. Modes that do not employ the electrochemically active molecule 5 therefore cannot perform accurate, high-sensitivity analysis as the present embodiment can.

Next, in the present embodiment, sample 10 is caused to migrate along the migration pathway interposed between the first electrode pair (the electrode 1a and the electrode 1b). That is, the sample 10 is caused to migrate between the first electrode pair (the electrode 1a and the electrode 1b). The magnitude of the first current flowing between the first electrode pair then changes according to the characteristics of the sample 10. Moreover, in the present embodiment, the first current flows at an artificially large value as described above, and the amount of change in the first current arising due to the sample 10 is therefore also large. As a result, high sensitivity analysis is therefore possible in the present embodiment of the sample 10. More detailed explanation of this point follows, with reference to FIG. 2A to FIG. 5B.

Figure 2A:
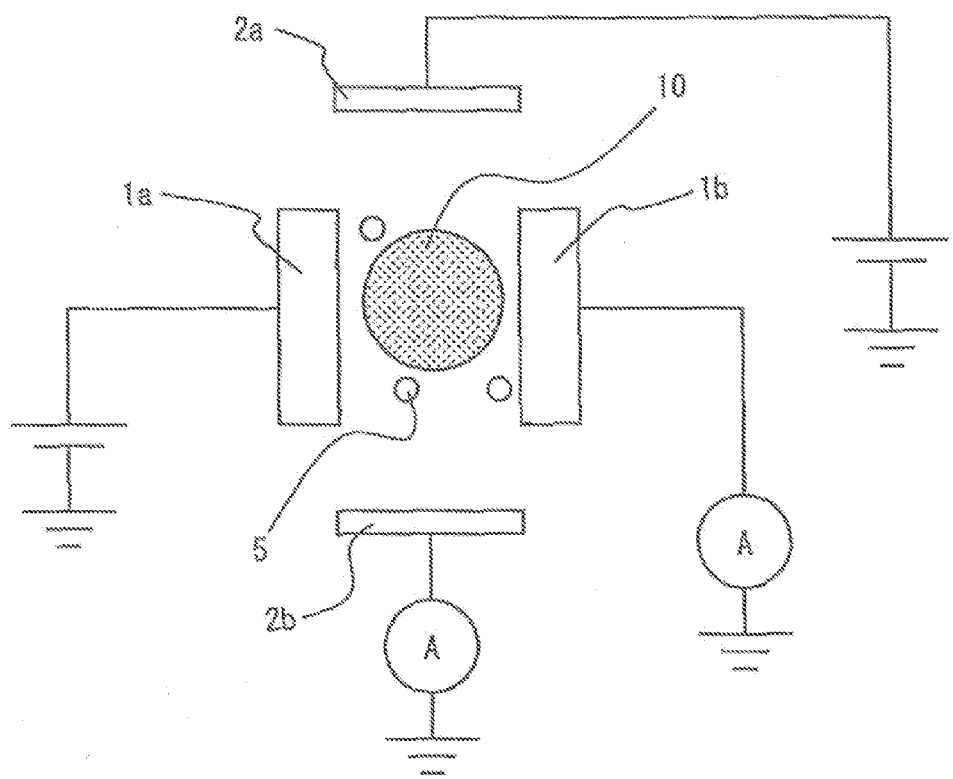
FIG. 2A is a diagram showing an analysis method of an embodiment of the invention.
Figure 2B:
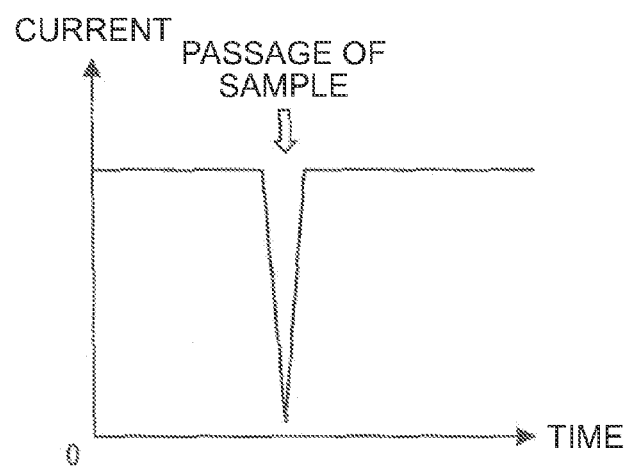
FIG. 2B is a diagram showing an analysis method of an embodiment of the invention.
Figure 3A:
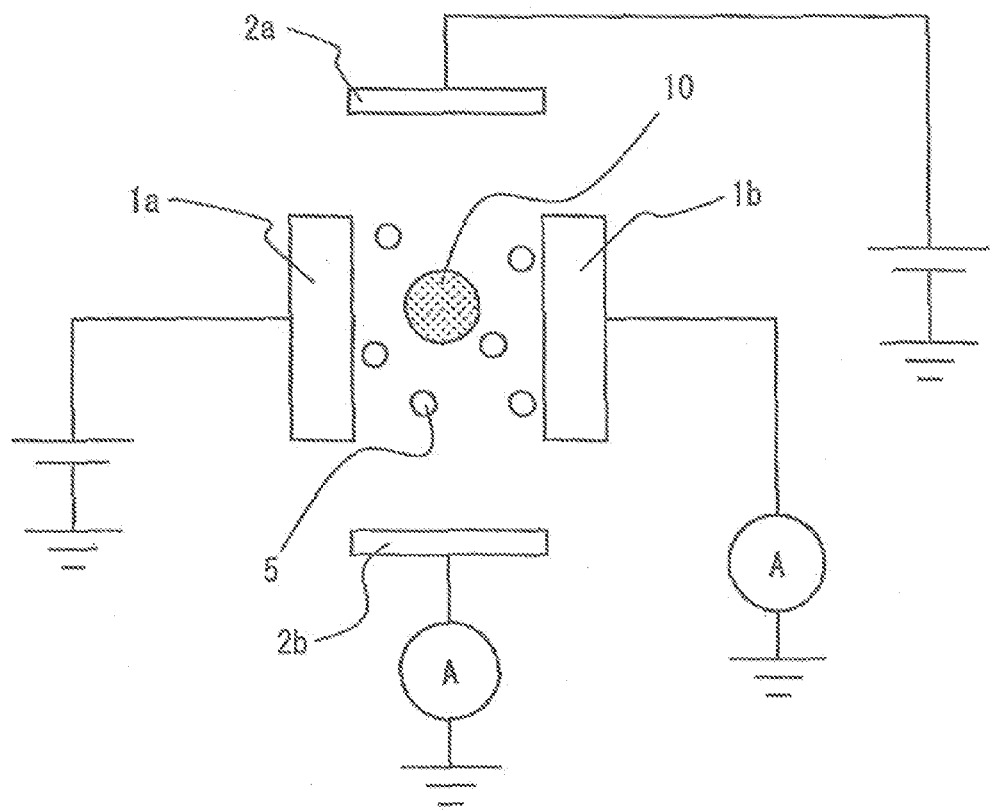
FIG. 3A is a diagram showing an analysis method of an embodiment of the invention.
Figure 3B:
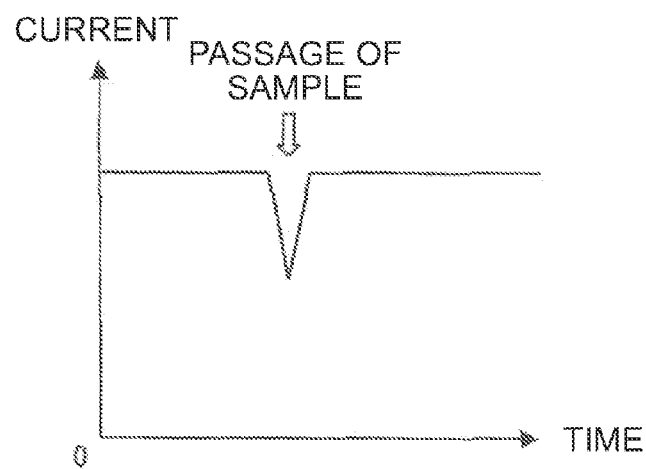
FIG. 3B is a diagram showing an analysis method of an embodiment of the invention.

FIG. 2A and FIG. 2B illustrate a change in the first current when a sample 10 of large volume migrates. FIG. 3A and FIG. 3B illustrate the change in the first current when a sample 10 of small volume migrates.

As illustrated in FIG. 2A, when the sample 10 of large volume migrates between the first electrode pair, the majority of the electrochemically active molecules 5 that were present between the first electrode pair are expelled from the space between the first electrode pair. In other words, when the sample 10 of large volume migrates between the first electrode pair, the number of the electrochemically active molecules 5 present between the first electrode pair changes greatly, and as a result, the number of the electrochemically active molecules 5 giving rise to the redox reaction changes greatly. As illustrated in FIG. 2B, the value of the current flowing between the first electrode pair then changes greatly.

However, as illustrated in FIG. 3A, a small number of the electrochemically active molecules 5 that were present between the first electrode pair is expelled from the space between the first electrode pair when the sample 10 of small volume migrates between the first electrode pair. In other words, when the sample 10 of small volume migrates between the first electrode pair, the number of electrochemically active molecules 5 present between the first electrode pair changes to a small extent, and as a result, the number of electrochemically active molecules 5 giving rise to the redox reaction changes to a small extent. As illustrated in FIG. 3B, the value of the first current flowing between the first electrode pair then changes to a small extent. Such small changes in current are detectable since a large value of the first current was already flowing to the first electrode pair.

As described above, the amount of change in the first current is correlated with the volume of the sample 10. Thus, information related to the volume of the sample 10 can be obtained by measuring the amount of change in the first current.

Figure 4A:
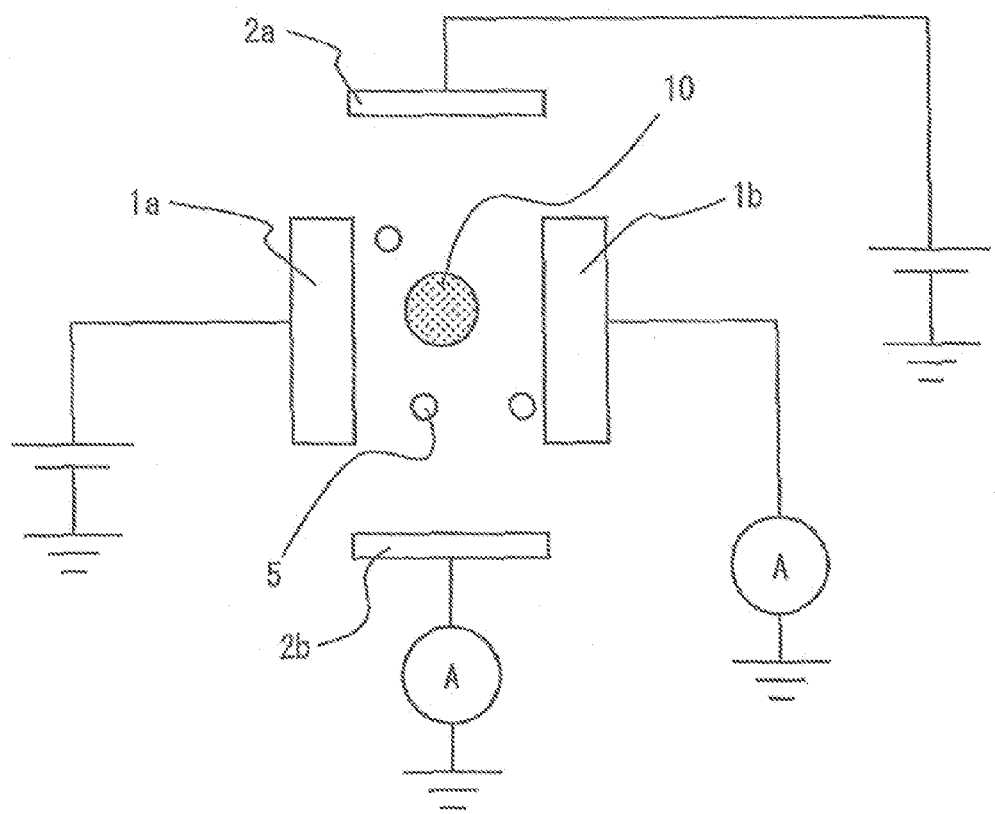
FIG. 4A is a diagram showing an analysis method of an embodiment of the invention.
Figure 4B:
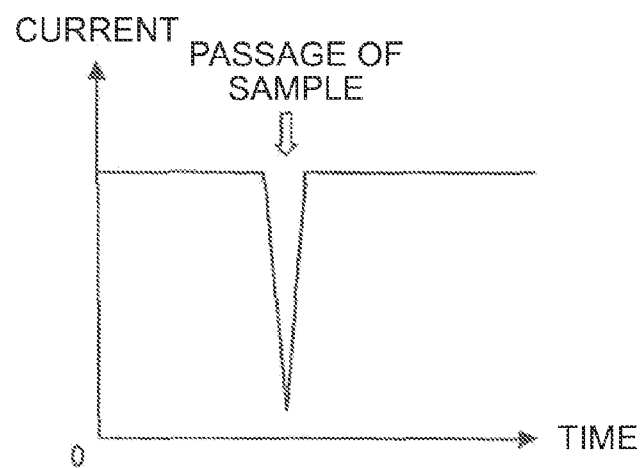
FIG. 4B is a diagram showing an analysis method of an embodiment of the invention.
Figure 5A:
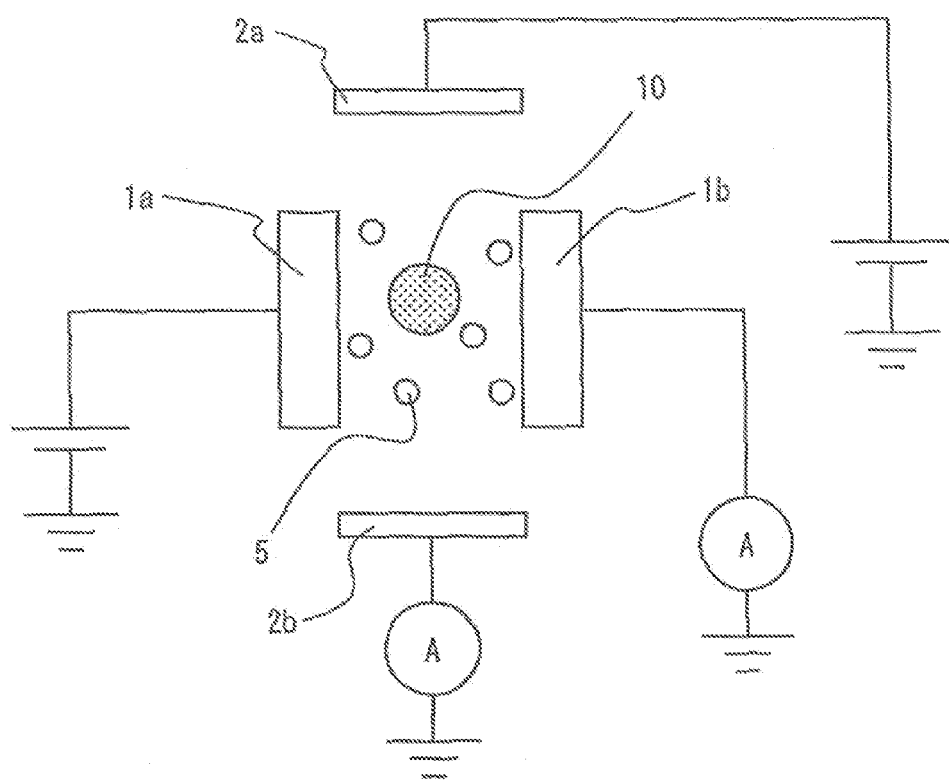
FIG. 5A is a diagram showing an analysis method of an embodiment of the invention.
Figure 5B:
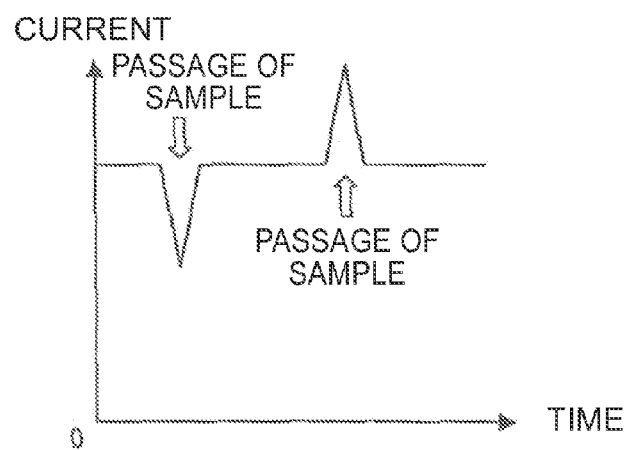
FIG. 5B is a diagram showing an analysis method of an embodiment of the invention.

FIG. 4A and FIG. 4B illustrate the change in the first current when the electrochemically active molecule 5 and the sample 10 have the same type of charge (a positive charge, or a negative charge) as each other. FIG. 5A and FIG. 5B illustrate the change in the first current when the electrochemically active molecule 5 and the sample 10 have different types of charge to each other.

As illustrated in FIG. 4A, when the electrochemically active molecule 5 and the sample 10 having the same type of charge migrate between the first electrode pair, the majority of the electrochemically active molecules 5 that were present between the first electrode pair are expelled by electrical repulsion from the space between the first electrode pair. In other words, when the electrochemically active molecule 5 and the sample 10 having the same type of charge migrate between the first electrode pair, the number of the electrochemically active molecules 5 present between the first electrode pair changes greatly, and as a result, the number of the electrochemically active molecules 5 giving rise to the redox reaction changes greatly. As illustrated in FIG. 4B, the value of the first current flowing between the first electrode pair then changes greatly. The greater the charge held by the electrochemically active molecule 5, the greater the amount of change in the first current tends to be.

However, as illustrated in FIG. 5A, when the electrochemically active molecule 5 and the sample 10, having a different type of charge to each other, migrate between the first electrode pair, either a small number of the electrochemically active molecules 5 that were present between the first electrode pair is expelled from the space between the first electrode pair, or the electrochemically active molecules 5 accumulate in the space between the first electrode pair due to electrical attraction. In other words, when the electrochemically active molecule 5 and the sample 10 having a different type of charge to each other migrate between the first electrode pair, the number of the electrochemically active molecules 5 present between the first electrode pair (in other words, the electrochemically active molecules 5 able to give rise to the redox reaction) either changes to a small extent, or increases. As a result, as illustrated in FIG. 5B, the value of the first current flowing between the first electrode pair changes to a small amount, or increases. The greater the charge held by the electrochemically active molecule 5, the larger the first current changes tend to be.

As described above, the amount of change in the first current is correlated with the type and the magnitude of the charge held by the sample 10. Thus, information related to the charge of the sample 10 can be obtained by measuring changes in the first current.

As illustrated in FIG. 1A to FIG. 5A, in the present embodiment, a voltage may be applied between a second electrode pair (an electrode 2a and an electrode 2b) formed so as to sandwich the migration pathway of the sample 10, such that an electric field is formed in a direction substantially parallel to the migration direction of the sample 10 (indicated by the arrow in FIG. 1).

In such cases, the second current, arising from ions migrating along the migration direction of the sample 10 within the migration pathway interposed between the first electrode pair, flows to the second electrode pair. The magnitude of the second current is correlated with the volume of the sample 10.

For example, as illustrated in FIG. 2A, when the sample 10 of large volume migrates between the first electrode pair, ion migration from the electrode 2a to the electrode 2b (or from the electrode 2b to the electrode 2a) is greatly hindered by the sample 10. As a result, the value of the second current flowing between the second electrode pair changes greatly (specifically, it decreases greatly).

However, as illustrated in FIG. 3A, when the sample 10 of small volume migrates between the first electrode pair, ion migration from the electrode 2a to the electrode 2b (or from the electrode 2b to the electrode 2a) is slightly hindered by the sample 10. As a result, the value of the second current flowing between the second electrode pair changes to a small extent (specifically, it decreases to a small extent).

As described above, the amount of change in the second current is correlated with the volume of the sample 10. Thus, information related to the volume of the sample 10 can be obtained by measuring the amount of change in the second current.

2. Sample Analysis Method

The sample analysis method of the present embodiment includes a first step to a fourth step. In addition to the first step to the fourth step, the analysis method of the present embodiment may further include one or more out of a fifth step to a seventh step. Explanation follows regarding each step.

2-1. First Step

The first step is a step of applying a voltage across the first electrode pair formed so as to sandwich the migration pathway of the sample, so that an electric field is formed in a direction intersecting the migration direction of the sample.

That is, in the present embodiment, the space between the anode and the cathode of the first electrode pair is the migration pathway of the sample. The electric field formed between the anode and cathode of the first electrode pair is formed in a direction intersecting the migration direction of the sample.

The angle of intersection is not particularly limited, as long as the electric field is formed intersecting the migration direction of the sample. For example, the electric field and the migration direction of the sample may intersect at an angle of from 45° to 90°, from 60° to 90°, from 70° to 90°, from 80° to 90°, or at 90°. The angle of intersection may of course be angles other than these, and this is not particularly limited.

Specific configurations of the first electrode pair are not limited, and suitable known electrodes may be employed. For example, gold electrodes, platinum electrodes, silver electrodes, copper electrodes, or organic conductive polymer electrodes (for example, polypyrrole) may be employed as the first electrode pair.

Of these, the first electrode pair is preferably gold electrodes or platinum electrodes. Adopting such a configuration enables the redox reaction of the electrochemically active molecules to be induced with greater stability at the first electrode pair. Moreover, such a configuration enables generation of gas at the first electrode pair to be more reliably suppressed. More detailed explanation of this point is given below in 2-2. Second Step.

The distance between the anode and the cathode of first electrode pair is not particularly limited, and it may be set as appropriate for the size of the sample. That is, it is sufficient for the distance between the anode and the cathode of the first electrode pair to be set to a distance allowing the passage of the sample to be analyzed.

For example, assume the sample is in the form of a sphere, and let Y (nm) be the diameter of that sphere. In such cases, it is sufficient for the distance X between the anode and the cathode of the first electrode pair to be longer than Y (nm) (Y<X).

In the present embodiment, current from the redox reaction of the electrochemically active molecule occurring at the surfaces of the first electrode pair flows between the first electrode pair. Since the generation of this current is not affected by the distance between the anode and the cathode of the first electrode pair, the distance between the anode and the cathode of the first electrode pair is not particularly limited.

However, the closer the volume of the space between the anode and the cathode of the first electrode pair is to the volume of the sample (in other words, the greater the ratio of volume occupied by the sample in the space between the anode and the cathode of the first electrode pair) the greater the amount of change tends to be in the first current flowing between the first electrode pair, and as a result, analytical sensitivity tends to increase. The maximum value of the distance X between the anode and the cathode of the first electrode pair may therefore be set to 100Y, 50Y, 20Y, 10Y, 8Y, 6Y, 4Y, 2Y, 1.5Y, or 1.2Y.

That is, the distance X between the anode and the cathode of the first electrode pair may be set such that Y<X<100Y, Y<X<50Y, Y<X<20Y, Y<X<10Y, Y<X<8Y, Y<X<6Y, Y<X<4Y, Y<X<2Y, Y<X<1.5Y, or Y<X<1.2Y. However, the present embodiment is not limited thereto.

More specifically, the distance X between the anode and the cathode of the first electrode pair may be 0.1 nm or greater, 0.5 nm or greater, 1 nm or greater, 2 nm or greater, or 10 nm or greater. Although the maximum value of the distance X is not particularly limited as explained above, it may be, for example, set to 50 nm or less, 100 nm or less, 500 nm or less, 1 μm or less, 5 μm or less, 10 μm or less, 20 μm or less, 50 μm or less, 100 μm or less, 200 μm or less, 500 μm or less, or 1 mm or less for each of the minima above.

In analysis based on tunneling current, the value of the tunneling current flowing between an electrode pair is small when the anode and the cathode of the electrode pair are a distance of 2 nm apart or greater, and analysis based on the tunneling current becomes problematic. However, since the analysis method of the present embodiment is an analysis method based on a completely different technical concept from analysis based on tunneling current, it is possible to perform analysis with excellent sensitivity even if, for example, the distance between the anode and the cathode of the first electrode pair is 2 nm or greater.

Taken from another perspective, the volume of the space between the anode and the cathode of the first electrode pair may be set such that the volume ratio occupied by one unit of the sample (for example, one molecule of the sample) in the space between the anode and the cathode of the first electrode pair is 1% or more, 10% or more, 20% or more, 30% or more, 40% or more, 50% or more, 60% or more, 70% or more, 80% or more, 90% or more, or 95% or more. When doing so, the greater the ratio of volume occupied, the more sensitive the analysis that can be performed.

The value of the voltage applied between the first electrode pair is not particularly limited, and it may be appropriately set according to the type of electrochemically active molecule employed so that the redox reaction of the electrochemically active molecule is produced. For example, the voltage may be set to from −10V to +10V, from −5V to +5V, or to −1V to +1V; however, there is no limitation thereto.

The sample employed in the present embodiment is not particularly limited. Examples of the sample include nucleic acids (DNA or RNA), amino acids, proteins, pollen, viruses, cells, organic molecules, and inorganic molecules; however, there is no limitation thereto.

In the present embodiment, it is possible to measure current with high sensitivity even under physiological conditions (for example, an aqueous solution having a pH of 6.0 to 8.0 containing 0.15M NaCl). This enables various biomolecules (for example, nucleic acids, amino acids, proteins, pollen, viruses, cells, or the like) to be analyzed under physiological conditions without damaging them.

The sample may hold a charge (for example, a surface charge). In such cases, information related to the type of charge of the sample, and the charge quantity of the sample can be obtained by employing an electrochemically active molecule having a charge.

The configuration explained above is a basic configuration for the first step; however, in addition to the basic configuration described above, the first step may further include applying a voltage between the second electrode pair formed so as to sandwich the migration pathway of the sample, such that an electric field is formed in a direction substantially parallel to the migration direction of the sample. That is, in the first step, another electric field may be formed by the second electrode pair so as to intersect the electric field formed between the first electrode pair.

Although the direction of the electric field formed between the second electrode pair is preferably substantially parallel to the migration direction of the sample, this does not need to be strictly parallel. For example, the direction of the electric field formed between the second electrode pair and the migration direction of the sample may differ by from 0° to 45°, may differ from 0° to 30°, may differ from 0° to 20°, may differ from 0° to 10°, may differ from 0° to 5°, or may differ from 0° to 2°. Moreover, there is no specific limitation to the value of this difference.

The specific configuration of the second electrode pair is not particularly limited, and suitable known electrodes may be employed therefor. For example, silver/silver chloride electrodes, gold electrodes, platinum electrodes, silver electrodes, copper electrodes, or organic conductive polymer electrodes (for example polypyrrole) may be employed as the second electrode pair.

Of these, a silver/silver chloride electrode is preferably employed as the second electrode pair. Such a configuration enables a second current, arising from ions that migrate along the migration direction of the sample within the migration pathway interposed by the first electrode pair (for example, chloride ions), to flow effectively between the second electrode pair, and with greater stability. More detailed explanation is given in 2-2. Second Step below.

The distance between the anode and the cathode of the second electrode pair is not particularly limited, and it may be set as appropriate. For example, the distance between the anode and the cathode of the second electrode pair is preferably 100 µm or less. This is because the diffusion effect of ions in the solution may affect the signal sensitivity (the signal sensitivity detected by the second electrode pair) when the distance is greater than 100 µm.

2-2. Second Step

The second step is a step of causing a first current arising from the redox reaction to flow to the first electrode pair by placing within the migration pathway interposed between the first electrode pair the solution including the electrochemically active molecule that produces the redox reaction at the first electrode pair. That is, the second step is a step of forming the baseline of the first current flowing between the first electrode pair.

The second step may be performed prior to the first step, may be performed simultaneously with the first step, and may, of course, be performed after the first step.

The solution may be placed so as to fill the space between the second electrode pair, in addition to filling the space between the first electrode pair.

Components other than the electrochemically active molecule may be included in the solution provided that they do not hinder the redox reaction arising at the first electrode pair.

For example, various buffers may be added to the solution and the solution pH may be controlled. The type of buffer is not particularly limited, and for example, buffers having low toxicity to living things and biomolecules, such as Tris buffer, MES buffer, PIPES buffer, MOPS buffer, or HEPES buffer, are preferably employed. The pH of the solution is not particularly limited, and for example, it may be from pH 6.0 to pH 8.0.

The present embodiment enables a large value of the first current to flow between the first electrode pair, without depending on the solution pH. That is, it is possible to perform physiological analysis of the sample under physiological conditions.

The solution may include chloride ions (for example, KCl, NaCl, $CaCl_2$, or the like) to allow current flow when the second electrode pair is silver/silver chloride electrodes. Such configuration enables the second current, arising from migration of chloride ions, to flow between the second electrode pair. Although not particularly limited, the concentration of chloride ions may, for example, be in a range of 0.1 mM to 5M, and is more preferably 1 mM to 1M. The concentration is preferably a concentration at which there is a large amplification effect of the ionic current, and at which the sample is not affected.

Specific composition of the electrochemically active molecule is not particularly limited, provided that it is one enabling a redox reaction to be produced at the first electrode pair. The electrochemically active molecule preferably does not produce gas via the redox reaction.

For example, the electrochemically active molecule may be a metal complex, a organometallic complex, or an organic molecule.

Examples of the metal complex include iron complexes (such as potassium hexacyanoferrate complex, ferrocenes (for example, hydroxyferrocene), iron porphyrin complexes, iron (III) chloride/iron (II) chloride, iron-phenanthroline complexes, or the like), ruthenium complexes (hexamine ruthenium complex chloride, ruthenocene, or the like), cobalt complexes (cobaltocene, cobalt porphyrin complex, or the like), and manganese, nickel, and copper complexes. Of these metal complexes, potassium hexacyanoferrate complex can be said to be preferable. This is because the product and the reactant thereof have low redox potentials and are both readily soluble and stable in water.

Examples of the organic molecule include benzoquinone, benzoquinone derivatives, tetracyanoquinodimethane (TCNQ), tetramethylphenylene diamine (TMPD), and tetrathiafulvalene (TTF). Of these organic molecules, TCNQ and benzoquinone derivatives can be said to be preferable as they are substances with low redox potentials and high solubility in water.

Moreover, the electrochemically active molecule preferably gives rise to a redox reaction when a voltage of −1V to 1V is applied.

The electrochemically active molecule employed in the present embodiment is not limited to those described above, and known electrochemically active molecules may be employed. For example, Documents X (science chronology tables/chemistry handbooks), and Document Y (A Bard, Electrochemical Methods Fundamentals and Applications, Wiley) describe various types of electrochemically active molecule, and these electrochemically active molecule may be employed in the present embodiment. Documents X and Document Y are incorporated herein by reference.

As described above, in the present embodiment, for current to flow between the second electrode pair, as described later, a chloride ion (for example, KCl, NaCl, $CaCl_2$, or the like) may be included in the solution placed in the migration pathway that is interposed between the first electrode pair. In such cases, due to the electrochemically active molecule being present in the solution, a redox reaction of the electrochemically active molecule occurs at the first electrode pair, and enables, as a result, a stable flow of the first current. Explanation follows regarding this point.

If no electrochemically active molecule is present in the solution, reactions like those below occur at the anode and the cathode of the first electrode pair, and as a result, gases (oxygen, chlorine, hydrogen, or the like) are generated.

Anode: $2Cl^- \rightarrow Cl_2 + 2e^-$   Reaction 1

Anode: $2H_2O \rightarrow O_2 + 4H^+ + 4e^-$   Reaction 2

Cathode: $2H_2O + 2e^- \rightarrow H_2 + 2OH^-$   Reaction 3

The gases adhere to the surfaces of the first electrode pair, and value of the current flowing between the first electrode pair becomes unstable.

However, when an electrochemically active molecule (for example, potassium hexacyanoferrate complex) is present in the solution, reactions like those below occur at the anode and the cathode of the first electrode pair, and as a result, gas is not generated. Such electrochemically active molecules are merely examples, and the present embodiment is not limited thereto.

Anode: $[Fe(CN)_6]^{4-} \rightarrow [Fe(CN)_6]^{3-} + e-$   Reaction 4

Cathode: $[Fe(CN)_6]^{3-} + e^- \rightarrow [Fe(CN)_6]^{4-}$   Reaction 5

When this occurs, a flow of electrodes is produced by Reaction 4 and by Reaction 5, to form the first current flowing between the first electrode pair.

Since potassium hexacyanoferrate complex and the like are formed with an ion that holds a negative charge, information related to the charge type and the charge quantity of the sample can be obtained based on the negative charge.

When the electrochemically active molecule (for example, hexaammineruthenium complex chloride) is present in the solution, reactions such as those below are produced at the anode and the cathode of the first electrode pair, and as a result, gas is not generated. This electrochemically active molecule is also merely an example, and the present embodiment is not limited thereto.

Anode: $[Ru(NH_3)_6]^{3+} \rightarrow [Ru(NH_3)_6]^{4+} + e^-$   Reaction 6

Cathode: $[Ru(NH_3)_6]^{4+} + e^- \rightarrow [Ru(NH_3)_6]^{3+}$   Reaction 7

When this occurs, a flow of electrons is produced by Reaction 6 and by Reaction 7, forming the first current flowing between the first electrode pair.

Since hexaammineruthenium complex chloride and the like are formed with an ion that holds a positive charge, information related to the charge type and the charge quantity of the sample can be obtained based on the positive charge.

The configuration explained above is a basic configuration for the second step; however, in addition to the basic configuration described above, the second step may further include causing a second current arising from ion migration along the migration direction of the sample to flow in the migration pathway interposed between the first electrode pair, to the second electrode pair by placing the solution including the electrochemically active molecule that produces the redox reaction at the first electrode pair within the migration pathway interposed between the first electrode pair.

As described above, the solution that includes the electrochemically active molecule may include a chloride ion (for example, KCl, NaCl, $CaCl_2$, or the like) in order for the second current to flow between the second electrode pair. The following reactions are then, for example, produced at the anode and the cathode of the second electrode pair when, for example, silver/silver chloride electrodes are employed as the second electrode pair. That is:

Anode: $Ag + Cl^- \rightarrow AgCl + e^-$   Reaction 8

Cathode: $AgCl + e^- \rightarrow Ag + Cl^-$   Reaction 9

The flow of ions (for example, chloride ions) produced by reaction 8 and by reaction 9 then forms a second current flowing between the second electrode pair.

2-3. Third Step

The third step is a step of causing the sample to migrate along the migration pathway interposed between the first electrode pair.

In this step, the number of electrochemically active molecules present within the space interposed between the first electrode pair changes with migration of the sample. For example, the number of the electrochemically active molecules is greatly diminished, slightly diminished, greatly increased, or slightly increased, according to the characteristics of the sample. The value of the current flowing between the first electrode pair and the second electrode pair then changes due to the change in the number of the electrochemically active molecules.

The driving force that causes the migration is not particularly limited. For example, the sample may be allowed to migrate by free diffusion, and the sample may be caused to migrate electrically by the second electrode pair.

The distance L over which the sample migrates along the migration pathway interposed between the first electrode pair (in other words, a length between the first electrode pair (the anode and the cathode) along the migration direction of the sample) is not particularly limited, and it may be set as appropriate.

From the viewpoint of accurately predicting the volume, the type of the charge, and the quantity of charge of the sample, a distance L that is longer than the length of the sample in its length direction, in other words a length sufficient to completely accommodate the whole sample in the space between the first electrode pair, can be described as preferable.

For example, the distance L may be 0.1 nm or greater, 0.5 nm or greater, 1 nm or greater, 2 nm or greater, or 10 nm or greater. Although the maximum value of the distance L is not particularly limited, for example, for each of the minima above, the maximum may be set to 50 nm or less, 100 nm or less, 500 nm or less, 1 nm or less, 5 nm or less, 10 nm or less, 20 nm or less, 50 nm or less, 100 nm or less, 200 nm or less, 500 nm or less, or 1 mm or less. The present embodiment is of course not limited thereto.

2-4. Fourth Step

The fourth step is a step of measuring the amount of change in the first current produced by migration of the sample. That is, the fourth step is a step of changing the number of electrochemically active molecules that are present in the space interposed between the first electrode pair with the migration of the sample, and measuring the amount of change in the first current produced thereby.

This step may be carried out by measuring the current flowing between the first electrode pair using a known ammeter.

The configuration explained above is a basic configuration for the fourth step; however, in addition to the basic configuration described above, the fourth step may further incorporate measurement of the amount of change in the second current produced by the migration of the sample.

This step may be carried out by measuring the current flowing between the second electrode pair using a known ammeter.

2-5. Fifth Step

In addition to the first step to the fourth step described above, the sample analysis method of the present embodiment may further include a fifth step.

The fifth step is a step of calculating the volume of a sample of unknown volume, from the amount of change in the first current for a sample with unknown volume, based on a correlation between the volume of reference samples and the amount of change in the first current.

In other words, the fifth step is a step of calculating the volume of the sample, this being an unknown volume, from the amount of change in the first current for the sample of unknown volume, based on a correlation between the volume of the reference samples and the amount of change in the first current, found in advance using reference samples of known volume according to the first step to the fourth step described above.

The correlation between the volume of the reference samples and the first current may be found by analyzing various reference samples of known volume according to the first step to the fourth step described above.

For example, suppose measurements using the first step to the fourth step indicate that the amount of change in the first current is A1 for a sample 1 that has a volume (or length of the diameter when the shape of the sample is considered to be a sphere) of V1, the amount of change in the first current is A2 for a sample 2 that has a volume of V2, the amount of change in the first current is A3 for a sample 3 that has a volume of V3, and the amount of change in the first current is A4 for a sample 4 that has a volume of V4.

Although four types of reference sample are employed in the case of this example, the number of reference samples is not particularly limited. However, in order to calculate the unknown sample volume with better precision, it can be said to be more preferable that the numbers of reference samples be greater.

Using V1 to V4 and A1 to A4 above, the volume V can be expressed as a function of the amount of change A in the first current according to known methods. The type of this function (for example, a first order function, a second order function, or the like) may be chosen so as to best approximate to actual measurement values for the reference samples.

When the amount of change in the first current is measured for the sample of unknown volume according to the first step to the fourth step, the volume of the sample of unknown volume can accordingly be calculated by substituting the measured value into the function.

Provided that the reference sample has a known volume, there are no particular limitations to the specific composition thereof. For example, polystyrene beads or the like may be employed as the reference sample.

2-6. Sixth Step

In addition to the first step to the fourth step, the sample analysis method of the present embodiment may further include a sixth step.

The sixth step is a step of calculating the quantity of charge of a sample of unknown charge quantity from the amount of change in the first current for the sample of unknown charge quantity, based on a correlation between the quantity of charge of reference samples and the amount of change in the first current.

In other words, the sixth step is a step of calculating the quantity of charge of the sample, this being of unknown charge quantity, from the amount of change in the first current for the sample of unknown charge quantity, based on a correlation between the quantity of charge of the reference sample and the amount of change in the first current, found in advance using reference samples of known charge quantity according to the first step to the fourth step described above.

The correlation between the quantity of charge of the reference samples and the amount of change in the first current may be found by analyzing various reference samples of known charge quantity according to the first step to the fourth step described above.

For example, suppose measurements using the first step to the fourth step indicate that the amount of change in the first current is A1 for a sample 1 that has a quantity of charge C1, the amount of change in the first current is A2 for a sample 2 that has a quantity of charge C2, the amount of change in the first current is A3 for a sample 3 that has a quantity of charge C3, and the amount of change in the first current is A4 for a sample 4 that has a quantity of charge C4.

Although four types of reference sample are employed in the case of this example, the number of reference samples is not particularly limited. However, in order to calculate the unknown sample quantity of charge to better precision, it can be said to be more preferable that the number of reference samples be greater.

Using C1 to C4 and A1 to A4 above, the charge quantity C can be expressed as a function of the amount of change A in the first current according to known methods. The type of this function (for example, a first order function, a second order function, or the like) may be chosen so as to best approximate actual measured values for the reference samples.

When the amount of change in the first current is measured for the sample of unknown charge quantity according to the first step to the fourth step, the quantity of charge of the sample of unknown charge quantity can accordingly be calculated by substituting the measured value into the function, and information related to the type of charge can be obtained.

Provided that the quantity of charge and the type of charge of the references samples are known, there are no particular limitations to the specific composition thereof. For example, chemically modified polystyrene beads, or chemically modified gold particles may be employed as the reference samples.

2-7. Seventh Step

In addition to the first step to the fourth step, the sample analysis method of the present embodiment may further include a seventh step.

The seventh step is a step of calculating the volume of a sample of unknown volume, from the amount of change in the second current for the sample of unknown volume, based on a correlation between the volume of reference samples and the amount of change in the second current.

In other words, the seventh step is a step of calculating the volume of the sample, this being an unknown volume, from the amount of change in the second current for the sample of unknown volume, based on a correlation between the volume of the reference samples and the amount of change in the second current, found in advance using the reference samples that have known volumes according to the first step to the fourth step described above.

The correlation between the volume of the reference samples and the second current may be found by analyzing various reference samples of known volume according to the first step to the fourth step described above.

For example, suppose measurements using the first step to the fourth step indicate that the amount of change in the second current is A1 for a sample 1 that has a volume (or the length of the diameter when the shape of the sample is considered to be a sphere) of V1, the amount of change in the second current is A2 for a sample 2 that has a volume of V2, the amount of change in the second current is A3 for a sample 3 that has a volume of V3, and the amount of change in the second current is A4 for a sample 4 that has a volume of V4.

Although four types of reference sample are employed in the case of this example, the number of reference samples is not particularly limited. However, in order to calculate the unknown sample volume with better precision, it can be said to be more preferable that the number of reference samples be greater.

Using V1 to V4 and A1 to A4 above, the volume V can be expressed as a function of the amount of change A in the second current according to known methods. The type of this function (for example, a first order function, a second order function, or the like) may be chosen so as to best approximate actual measured values for the reference samples.

When the amount of change in the second current is measured for the sample of unknown volume according to the first step to the fourth step, the volume of the sample of unknown volume can accordingly be calculated by substituting the measured value into the function.

Provided that the reference sample has a known volume, there are no particular limitations to the specific composition thereof. For example, polystyrene beads or the like may be employed as the reference sample.

EXAMPLE

1. Explanation of Each Measurement Method 1-1. PC Electrical Measurement

Each type of measurement and analysis was performed using the LabVIEW program (NI PXIe system). The specific methods used protocols included in the program.

Specifically, I-V measurements (current-voltage measurements) and I-t measurements (current-time measurements) were performed at 10 kHz to 1 MHz. The I-V measurements were performed after confirming that the steady-state current had transitioned to a stable range for a fixed period of time.

1-2. Current Measurements Using the Second Electrode Pair

Buffer solutions of 1 mM to 100 mM, and electrochemically active molecules at 1 mM to 100 mM were employed in the current measurement.

A phosphoric acid buffer solution controlled to be pH 6.5 to pH 8.0, a 0.5× diluted TE buffer, a 0.5× diluted TBE buffer or the like, were employed as the buffer solution. The buffer solution can be described as a buffer solution that is close to physiological conditions.

Since the signal from the second electrode pair is a signal produced by ion charge transport being interrupted at an opening section of a hole (the space between the first electrode pair), this signal is a signal represented by diminished current values (a negative signal).

1-3. Current Measurements Using the First Electrode Pair

A buffer solution of 1 mM to 100 mM, and an electrochemically active molecule at 1 mM to 100 mM were employed in the current measurement.

A phosphoric acid buffer solution controlled to be pH 6.5 to pH 8.0, a 0.5× diluted TE buffer, a 0.5× diluted TBE buffer, or the like were employed as the buffer solution. The buffer solution can be described as a buffer solution that is close to physiological conditions.

Electrochemically active molecules that give rise to a redox reaction at low potentials (−1V to 1V) were employed so that the current could be measured stably. For example, when 10 mM potassium ferricyanide/potassium ferrocyanide was employed as the electrochemically active molecule, the value of the current flowing between the first electrode pair was $10^3$ times greater than in cases in which the electrochemically active molecule was not employed, and the strength of the measured signal was increased.

When analyzing a negatively charged sample (for example, a particle) using, for example, potassium ferricyanide/potassium ferrocyanide (an electrochemically active molecule having a negative charge), the signal from the first electrode pair is a signal represented by diminished current values (a negative signal) due to redox reactions being hindered in the electrode vicinity.

However, the signal increases when analyzing a sample (for example, a particle) having a negative charge of the same magnitude, using for example hexaammineruthenium chloride (an electrochemically active molecule having a positive charge). It is therefore apparent that the signal obtained reflects the charge state of the sample. Although the current that forms the background is stable when the electrochemically active molecule is added, the current becomes unstable when the electrochemically active molecule is not added.

2. Analytical Device Manufacture

An analytical device schematically illustrated in FIG. 1A was manufactured. Explanation follows regarding the manufacturing method of the analytical device.

2-1. Manufacture of a Solid State Nanopore Device

In the present example, a solid-state nanopore device was manufactured that includes a $SiO_2$ membrane structure and has a silicon substrate base, and the device was employed as a portion of the structure of the analytical device.

The solid-state nanopore device was manufactured primarily using electron beam lithography, deep reactive ion etching (RIE), or various types of etching (for example, etching employing a KOH solution).

Figure 6:
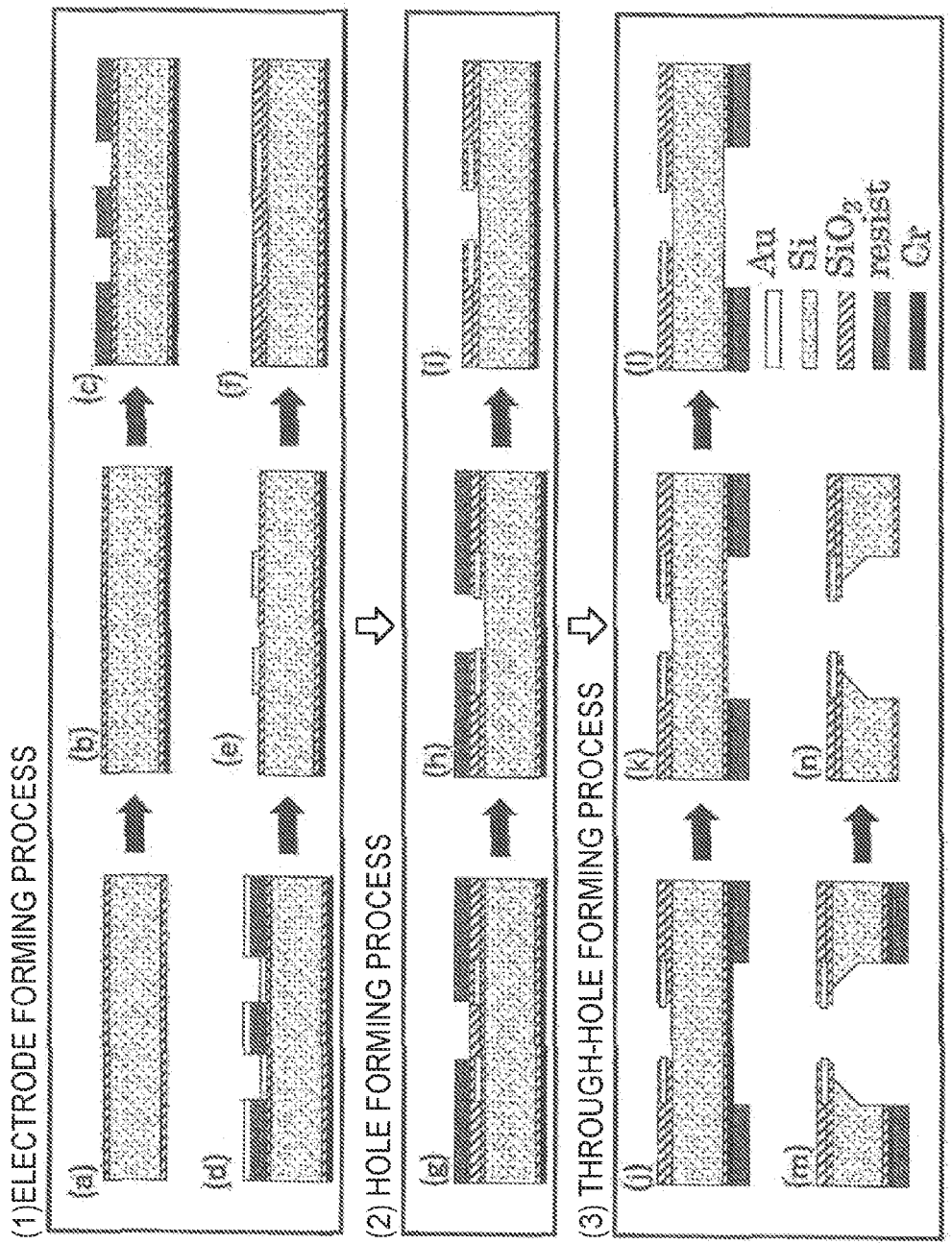
FIG. 6 is a diagram showing a manufacturing step of an analytical device of an example.

Specifically, as illustrated in (a) to (f) of FIG. 6, an $SiO_2$ membrane in which a pair of Au electrodes (corresponding to the first electrode pair) was embedded was first formed on a Si substrate. That is, an Au electrode pair having an extremely small interelectrode distance (for example, nanometer-size) was formed using this step.

Next, as illustrated in (g) to (i) of FIG. 6, a hole between the Au electrode pair (a space between the Au electrode pair) was formed by removing the $SiO_2$ membrane present between the Au electrode pair.

Moreover, as illustrated in (j) to (n) of FIG. 6, the hole was made to pierce through by removing the Si substrate present below the hole.

Next, lead wires from the Au electrode pair included in the solid-state nanopore device were manufactured by photolithography and Au sputtering. The lead wires connect to an ammeter or a voltage application device.

As described above, solid state nanopore devices provided with holes having various cross-section diameters (for example, from 0.05 μm to 200 μm) and depths (for example, from 0.05 μm to 50 μm) were manufactured.

2-2. Microchannel Manufacture

Microchannels were manufactured to introduce the sample into the hole formed between the Au electrode pair.

First, a microchannel mold was formed from SU-8 using photolithography, and polydimethylsiloxane (PDMS) was transferred into the mold. A PDMS substrate formed with microchannels was thereby manufactured.

The solid-state nanopore device and the PDMS substrate were pressure bonded using an acrylic holder so that the hole and the microchannels were connected. A connecting portion was formed on the acrylic holder in order to electrically connect the hole connected to a syringe pump to the first electrodes or the second electrodes.

2-3. Second Electrode Pair Manufacture

The second electrode pair was manufactured as Ag/AgCl electrodes using an Ag/AgCl paste (BAS Inc.). The specific manufacturing method was based on a known method.

3. Confirmation of Hole Characteristics-1

The characteristics of the nanosize holes manufactured under heading 2. Analytical Device Manufacture, were confirmed using a microscope.

FIG. 7A to FIG. 7D show photographs of the solid-state nanopore device taken through a microscope.

Figure 7A:
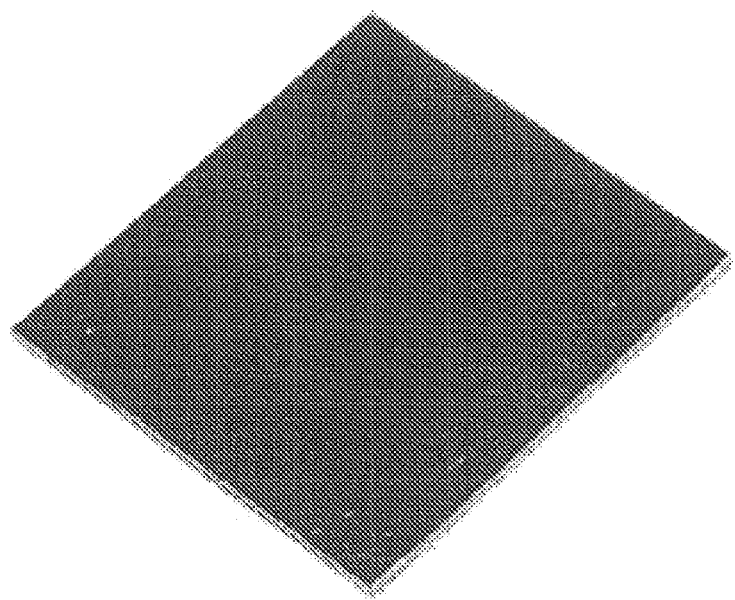
FIG. 7A is a photograph of a solid-state nanopore device taken through a microscope in an example.

FIG. 7A is a photograph of the solid-state nanopore device overall, taken using an optical microscope. The shape of the solid-state nanopore device overall was a plate shape of approximately 1 cm×1 cm. The hole was then formed in the central region of the solid-state nanopore device.

Figure 7B:
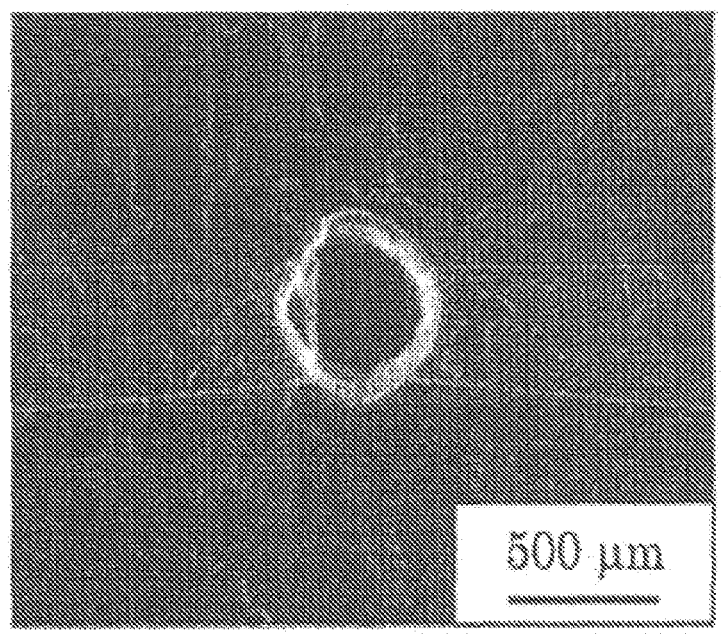
FIG. 7B is a photograph of a solid-state nanopore device taken through a microscope in an example.
Figure 7C:
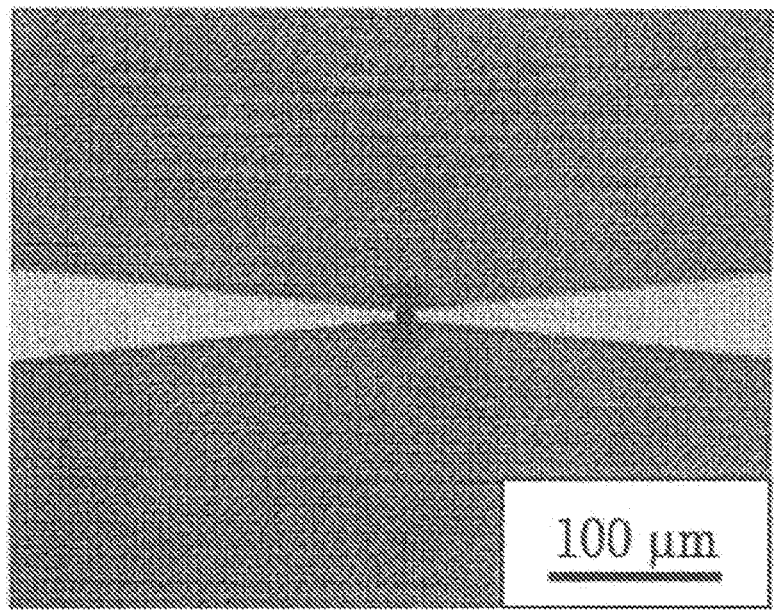
FIG. 7C is a photograph of a solid-state nanopore device taken through a microscope in an example.
Figure 7D:
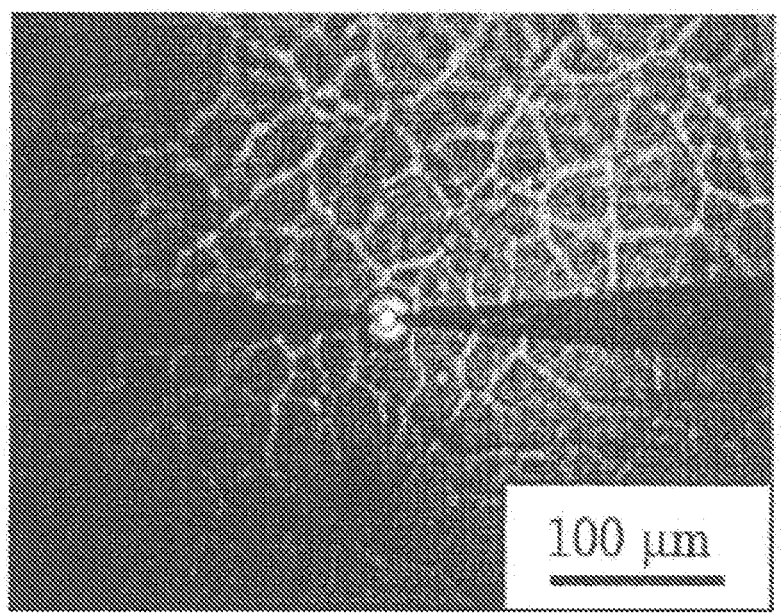
FIG. 7D is a photograph of a solid-state nanopore device taken through a microscope in an example.

FIG. 7C and FIG. 7D respectively illustrate a dark-field image and a bright-field image of a hole using an optical microscope. Based on these observations, it was confirmed that the holes had pierced through.

FIG. 7B shows an image of an even smaller hole, observed with a scanning electron microscope. From these observations the smaller hole was confirmed to have pierced through.

4. Confirmation of Hole Characteristics-2

The characteristics of the nanosized holes manufactured under heading 2. Analytical Device Manufacture, were confirmed using ionic current measurements employing an electrolytic solution (a KCl solution).

Figure 8A:
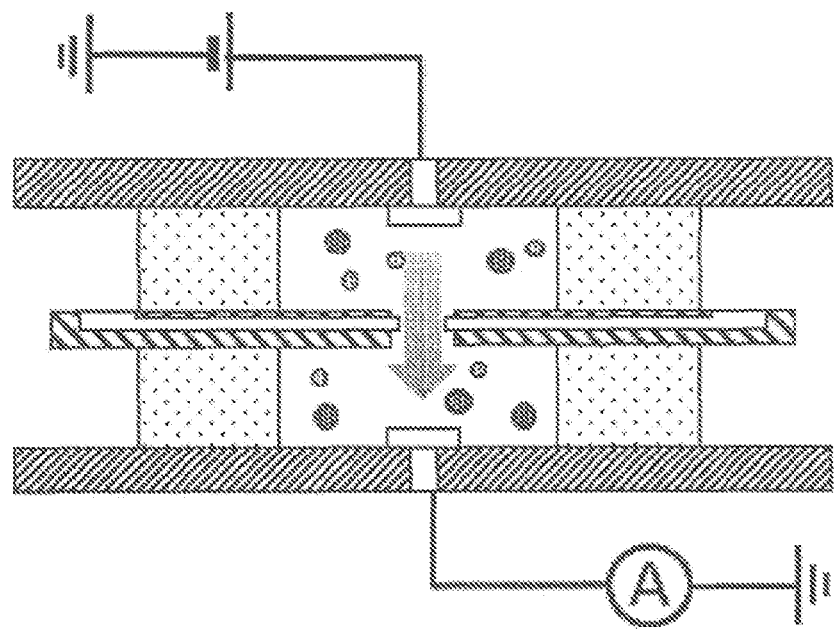
FIG. 8A is a diagram showing a configuration of an analytical device in an example.
Figure 8B:
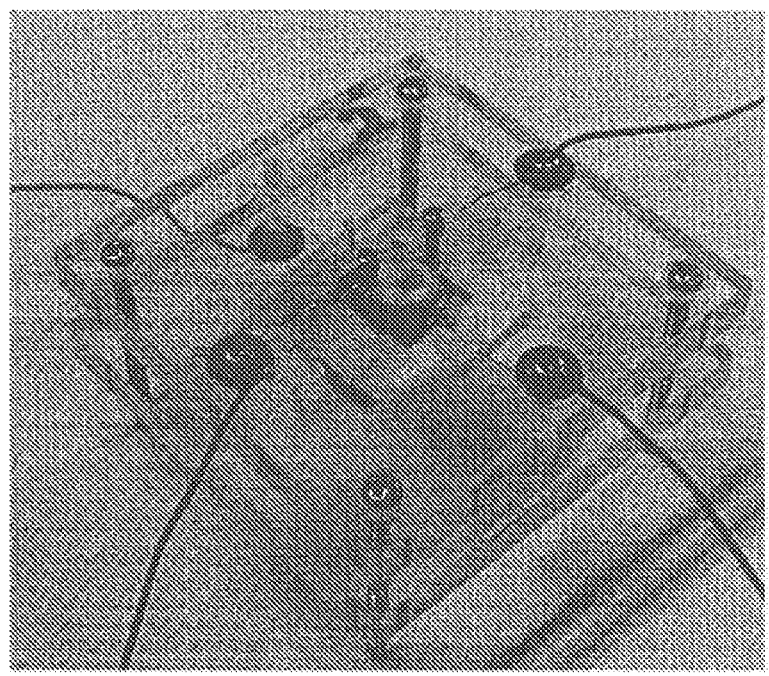
FIG. 8B is a diagram showing a configuration of an analytical device in an example.
Figure 8C:
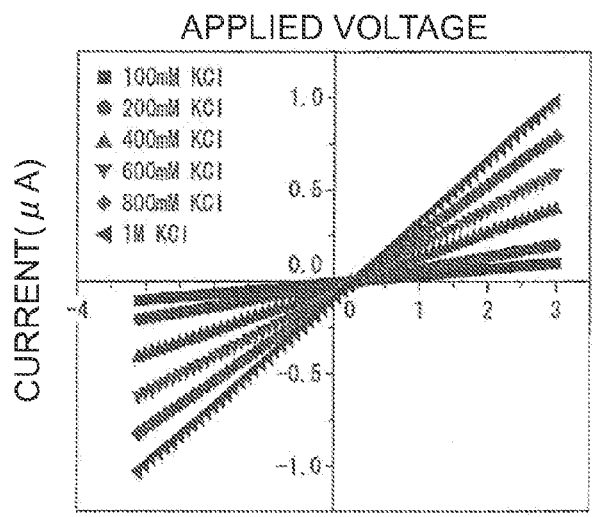
FIG. 8C is a graph showing characteristics of a hole provided to an analytical device in an example.
Figure 8D:
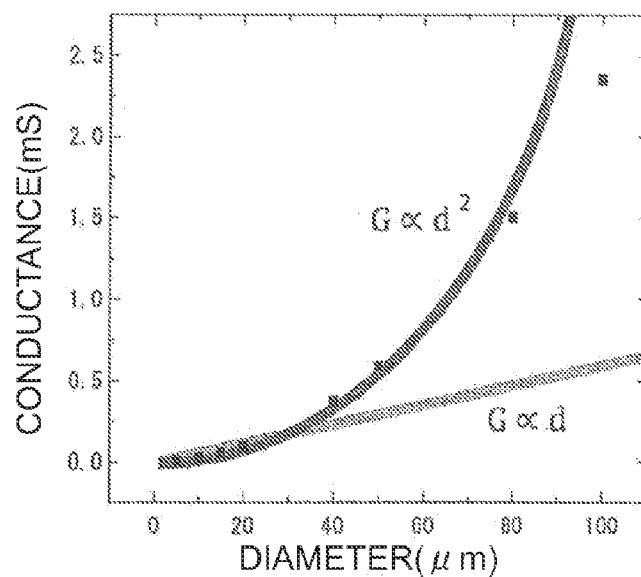
FIG. 8D is a graph showing characteristics of a hole provided to an analytical device in an example.
Figure 8E:
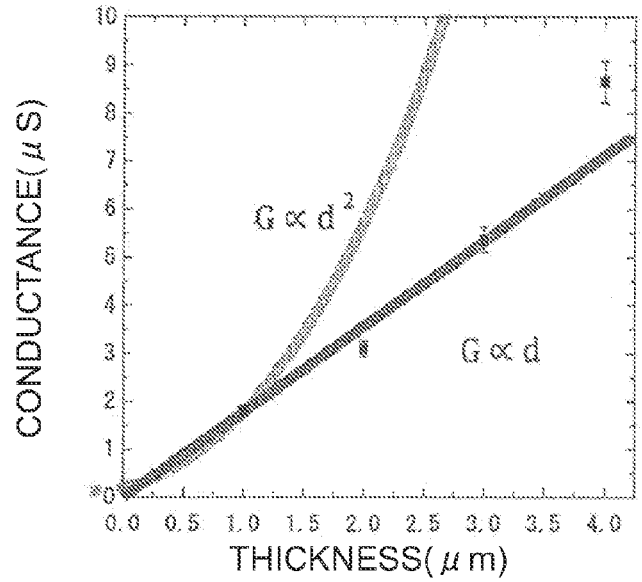
FIG. 8E is a graph showing characteristics of a hole provided to an analytical device in an example.

Specifically, FIG. 8A is a diagram showing a schematic of the analytical device. FIG. 8B is a photograph of the analytical device. In FIG. 8C to FIG. 8E, measurements of current flowing between the second electrode pair were made according to the method explained under section 1. Explanation of Each Measurement Method.

In FIG. 8C, values of current are plotted when the voltage applied between the second electrode pair was changed. The measurements results illustrated in FIG. 8C were obtained by introducing electrolyte solutions (KCl) at concentrations of "100 mM", "200 mM", "400 mM", "600 mM", "800 mM", and "1M" into a hole 60 µm in size. It is apparent from FIG. 8C that the holes exhibit Ohmic characteristics.

FIG. 8D shows the relationship between the cross-section diameter of the hole and conductance. It is apparent from FIG. 8D that the conductance depends on the cross-section diameter of the hole. FIG. 8E shows the relationship between the thickness of the hole and the conductance when the thickness of the membrane (L) is sufficiently small compared to the thickness of the hole (d) (when L<<d). As illustrated in FIG. 8E, the conductance is proportional to the square of the diameter of the hole when the thickness of the hole (d) is large, and the conductance is proportional to the diameter of the hole when the thickness of the hole (d) is small. It is therefore apparent that the electrical conductivity is dependent on the hole thickness.

That is, it can be confirmed from FIG. 8C to FIG. 8E that the device manufactured in the present example can function appropriately as an analytical device.

5. Analysis of the Characteristics of Current Flowing Between the Second Electrode Pair-1

The change in current flowing between the second electrode pair, arising when samples of various sizes (specifically, polystyrene beads with diameters of 2 µm, 4 µm, 6 µm, 10 µm, 40 µm, and 80 µm) were introduced into a nanosize hole (cross-section diameter of the hole: 200 µm, depth of the hole: 50 µm) produced as described under the heading 2 Analytical Device Manufacture, were measured. These measurements were confirmed using ionic current measurements employing an electrolytic fluid (KCl solution).

Figure 9A:
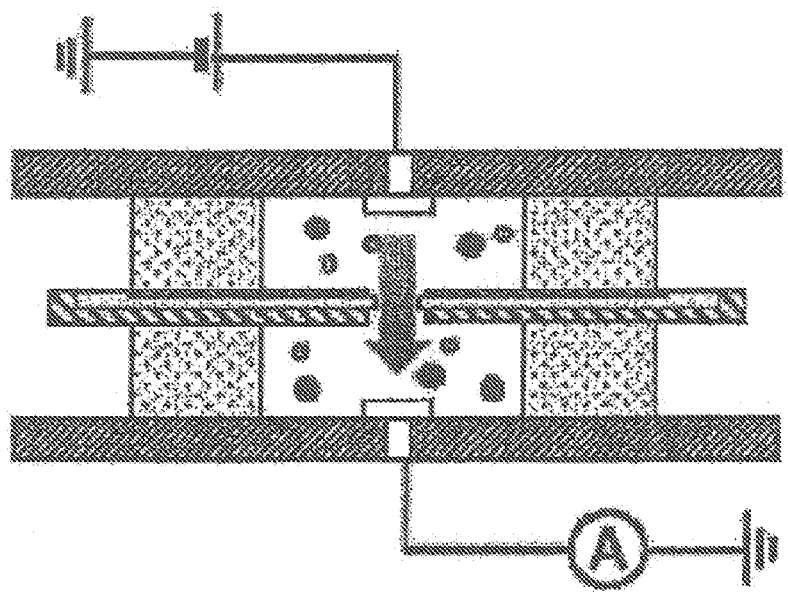
FIG. 9A is a diagram showing a configuration of an analytical device of an example.

FIG. 9A is a diagram showing a schematic of the analytical device.

Figure 9B:
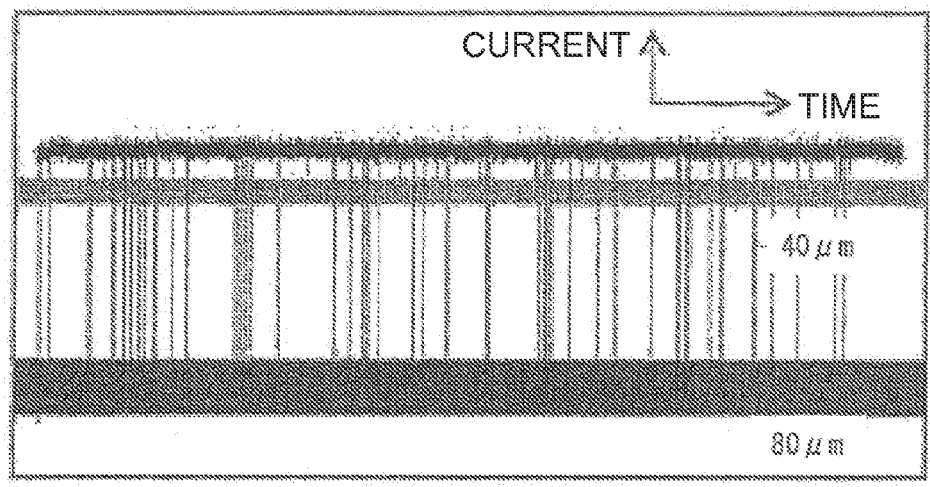
FIG. 9B is a graph showing characteristics of current flowing between a second electrode pair.
Figure 9C:
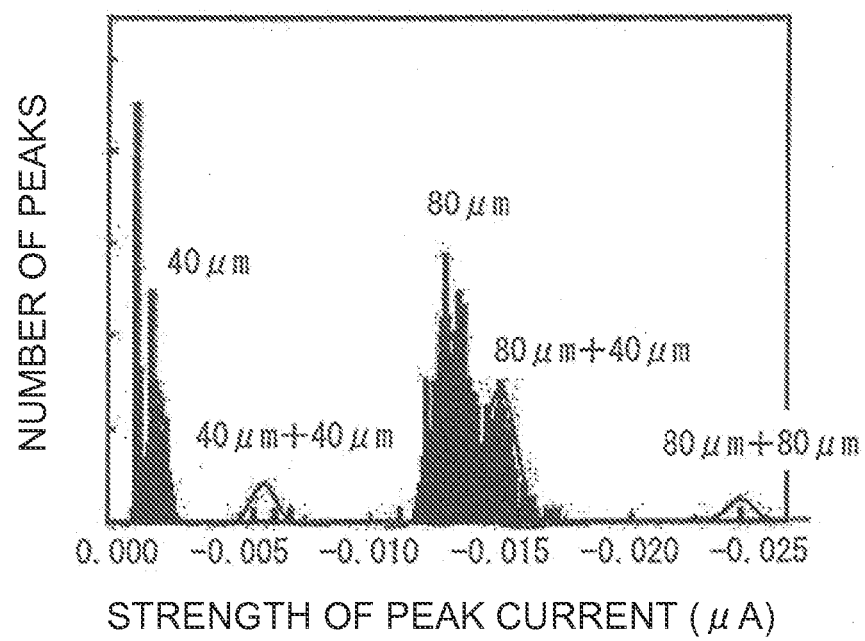
FIG. 9C is a graph showing characteristics of current flowing between a second electrode pair.

FIG. 9B shows the actual measured current when polystyrene beads having diameters of 40 µm or 80 µm were employed, and FIG. 9C shows the relationship between the resulting strength of the peak current and the number of peaks.

Figure 9D:
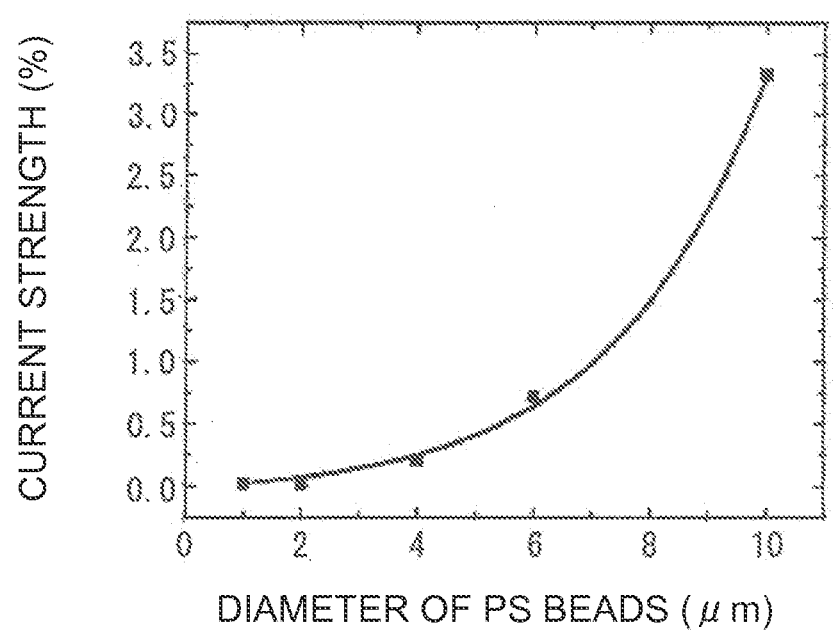
FIG. 9D is a graph showing characteristics of current flowing between a second electrode pair.

FIG. 9D shows the relationship between the strength of the peak current and the diameter of the beads when polystyrene beads having diameters of 2 µm, 4 µm, 6 µm, or 10 µm were employed.

As illustrated in FIG. 9D, it is apparent that there is a correlation between the size of the sample and the current flowing between the second electrode pair.

This demonstrates that when the change in current flowing between the second electrode pair is measured using an unknown sample, the diameter of the sample when the sample is considered to be a spherical bead can, for example, be calculated from the graph illustrated in FIG. 9D. If the diameter can be calculated, the volume of the sample can also be calculated.

6. Analysis of the Characteristics of Current Flowing Between the Second Electrode Pair-2

The change in current flowing between the second electrode pair, produced when polystyrene beads were introduced as the sample to the nanosize hole (cross-section diameter of the hole: 10 µm, depth of the hole: 10 µm) manufactured as described under the heading 2. Analytical Device Manufacture, were measured. This measurement employed PBS containing 10 mM $K_4[Fe(CN)_6]$/$K_3[Fe(CN)_6]$.

Figure 10A:
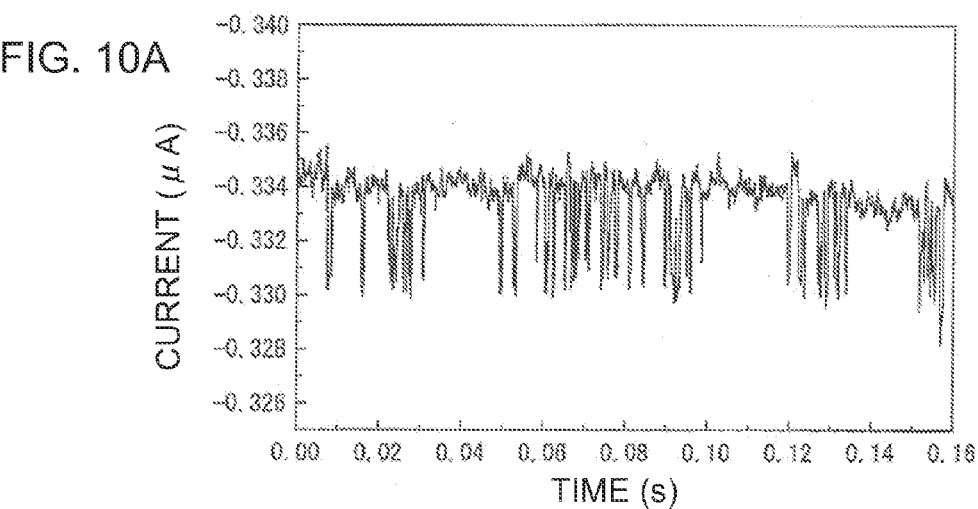
FIG. 10A is a graph showing characteristics of current flowing between a second electrode pair.

FIG. 10A is a graph showing the relationship between the current and time when polystyrene beads having a diameter of 8 µm were employed as the sample.

Figure 10B:
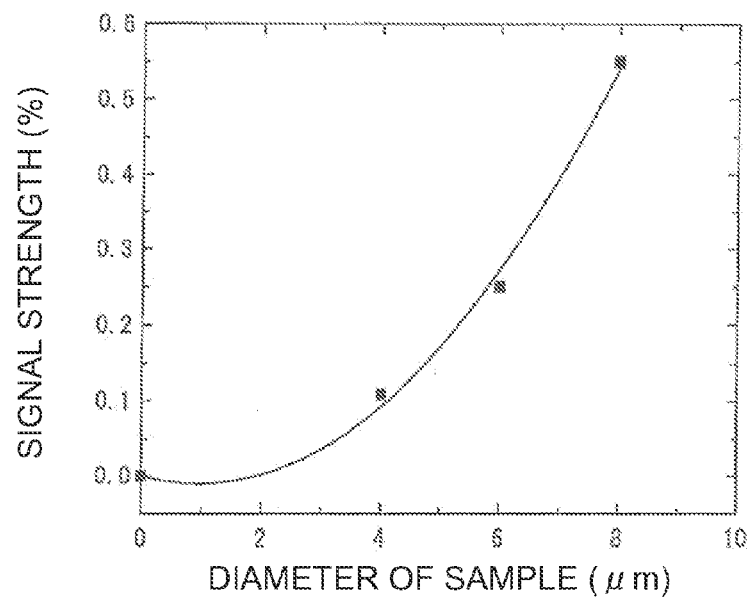
FIG. 10B is a graph showing characteristics of current flowing between a second electrode pair.

FIG. 10B is a graph showing the relationship between the signal strength and the diameter of the sample when polystyrene beads having diameters of 4 µm, 6 µm, or 8 µm were employed as the sample.

Figure 10C:
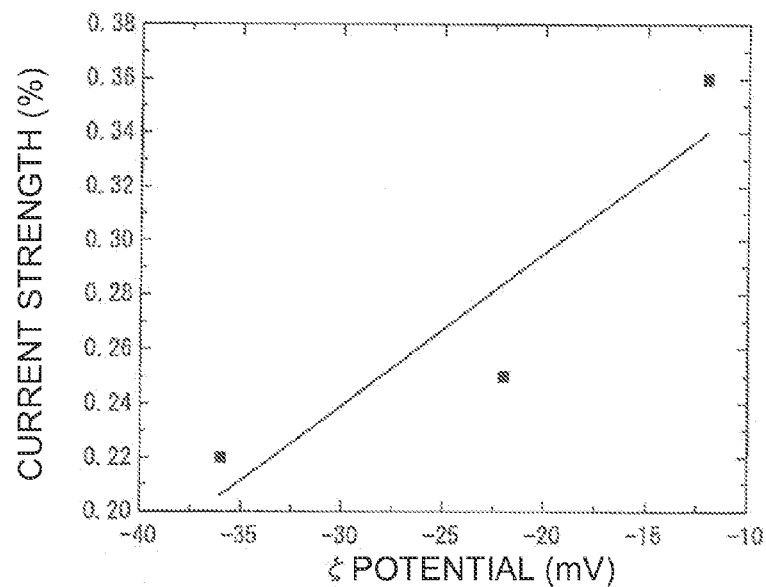
FIG. 10C is a graph showing characteristics of current flowing between a second electrode pair.

FIG. 10C is a graph showing the relationship between the current strength and the surface charge when polystyrene beads having a diameter of 6 µm were employed as the sample.

It is apparent from FIG. 10A to FIG. 10C that the signal strength is correlated with the diameter of the sample, and the current strength is correlated with the surface charge of the sample.

7. Analysis of Characteristics of the Current Flowing Between the First Electrode Pair-1

The current flowing between the first electrode pair (the base current flowing when no sample has been introduced) when an electrochemically active molecule (10 mM potassium ferricyanide/potassium ferrocyanide) is employed was compared with the current flowing between the first electrode pair when no electrochemically active molecule is employed.

Figure 11A:
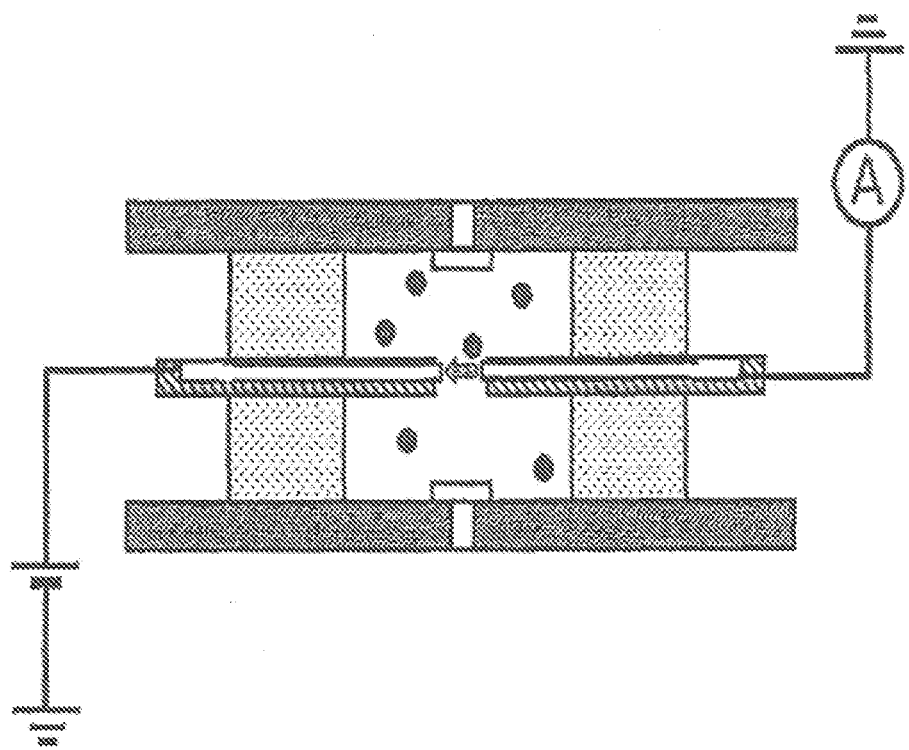
FIG. 11A is a diagram showing a configuration of an analytical device in an example.

FIG. 11A is a diagram showing a schematic of the analytical device.

Figure 11B:
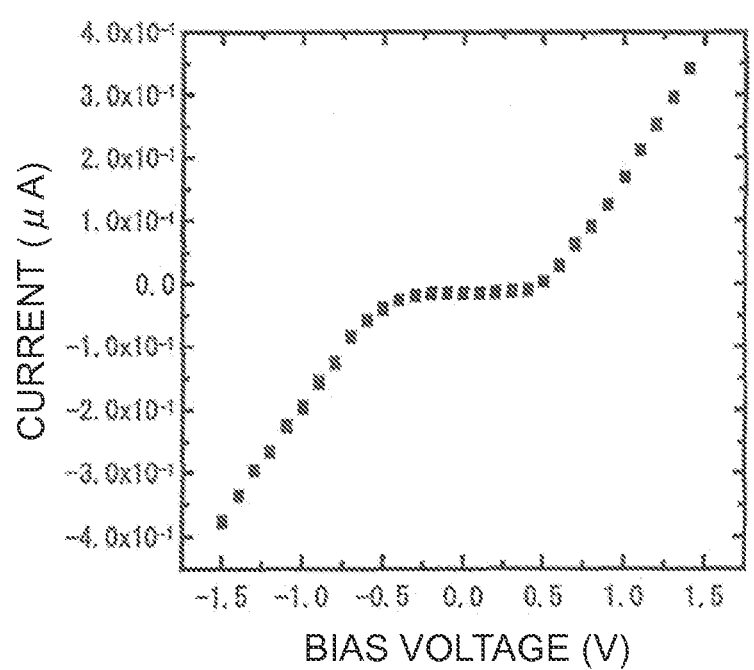
FIG. 11B is a graph showing characteristics of current flowing between a first electrode pair.

FIG. 11B shows the current-voltage characteristic when no electrochemically active molecule is employed.

Figure 11C:
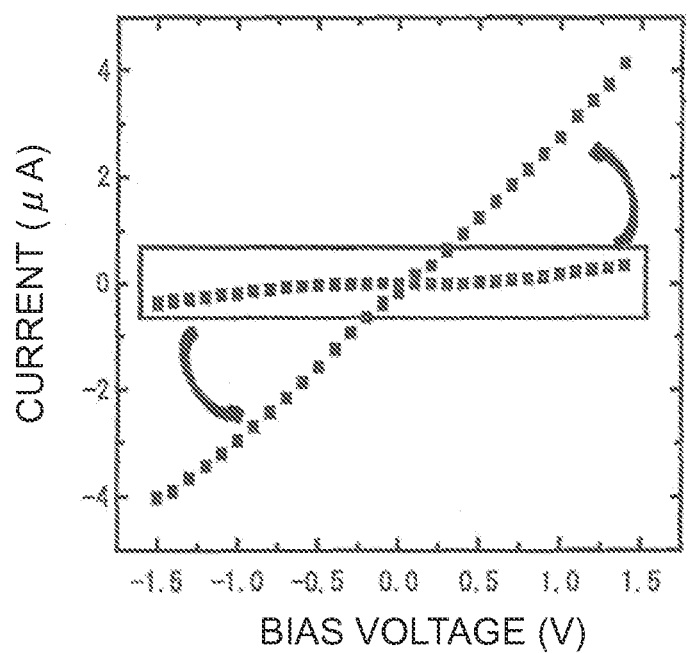
FIG. 11C is a graph showing characteristics of current flowing between a first electrode pair.

FIG. 11C shows the current-voltage characteristic when the electrochemically active molecule is employed. The data illustrated in the rectangular box in FIG. 11C shows the current-voltage characteristic when no electrochemically active molecule is employed.

The signal sensitivity was increased at a low potential at which stable electrical measurements are possible (−1V to +1V). For example, when 10 mM potassium ferricyanide/potassium ferrocyanide was employed as the electrochemically active molecule, the value of the current flowing between the first electrode pair was increased by a factor of approximately $10^3$, and the strength of the measured signal was increased.

When, for example, potassium ferricyanide/potassium ferrocyanide (a negatively charged electrochemically active molecule) was employed and a particle having a negative charge was analyzed, the signal from the first electrode pair was a signal represented by diminished current values (a negative signal) due to redox reactions being hindered in the vicinity of the electrodes.

However, when, for example, hexaammineruthenium chloride (an electrochemically active molecule having a positive charge) was employed and a particle having a negative charge of the same magnitude was analyzed, the signal increased. It is apparent from this that a signal was obtained that reflects the charge state of the particle.

Figure 11D:
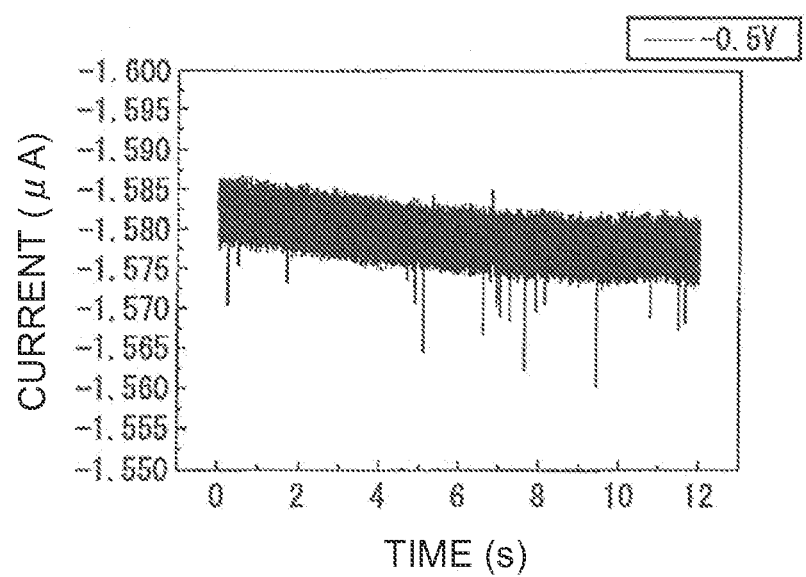
FIG. 11D is a graph showing characteristics of current flowing between a first electrode pair.
Figure 11E:
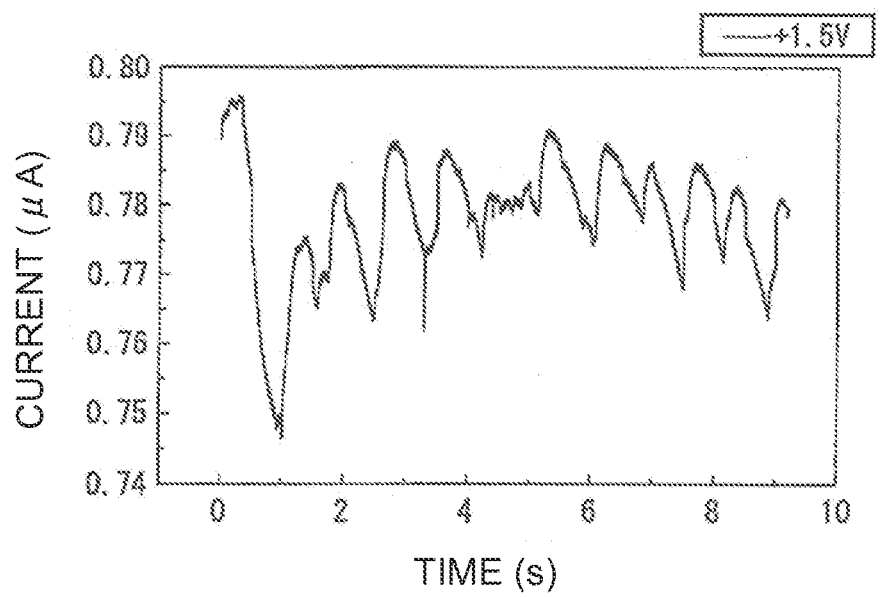
FIG. 11E is a graph showing characteristics of current flowing between a first electrode pair.
Figure 11F:
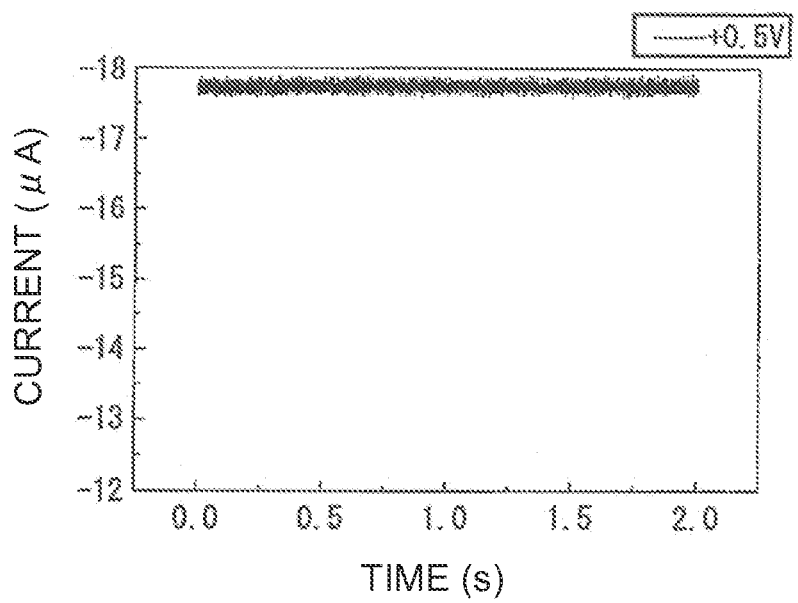
FIG. 11F is a graph showing characteristics of current flowing between a first electrode pair.

Moreover, although the background current was stable when the electrochemically active molecule was added (see FIG. 11D), the background current was either unstable or undetectable when the electrochemically active molecule was not added (see FIG. 11E and FIG. 11F).

Specifically, FIG. 11D shows the change produced in the current flowing between the first electrode pair when polystyrene beads (diameter 6 μm) were introduced as the sample into the nanosize hole (hole cross-section diameter: 10 μm, hole depth: 10 μm) manufactured as described under the heading 2. Analytical Device Manufacture. This measurement employed PBS including 10 mM $K_4[Fe(CN)_6]/K_3[Fe(CN)_6]$.

FIG. 11E and FIG. 11F illustrate the change produced in the current flowing between the first electrode pair when no sample is introduced into the nanosize hole (hole cross-section diameter: 10 μm, hole depth: 10 μm) manufactured as described under the heading 2. Analytical Device Manufacture. This measurement employed PBS.

8. Analysis of Characteristics of Current Flowing Between the First Electrode Pair-2

The current flowing between the first electrode pair was measured when various biological samples (for example, pollen (Japanese cedar and Japanese cypress pollen), blood cells (red blood cells and white blood cells), and viruses (adenovirus)) were employed.

Specifically, 10 mM potassium ferricyanide/potassium ferrocyanide was employed as the electrochemically active molecule. Moreover, 1x diluted PBS was employed as the solution to allow dispersion of the sample. The cross-section diameter of the hole (in other words, the interelectrode distance of the first electrode pair) was set to a length according to the size of the sample. Specifically, the cross-section diameter of the hole was set to 200 μm when pollen was employed as the sample, the cross-section diameter of the hole was set to 50 μm when blood cells were employed as the sample, and the cross-section diameter of the hole was set to 200 nm when a virus was employed as the sample.

Figure 12A:
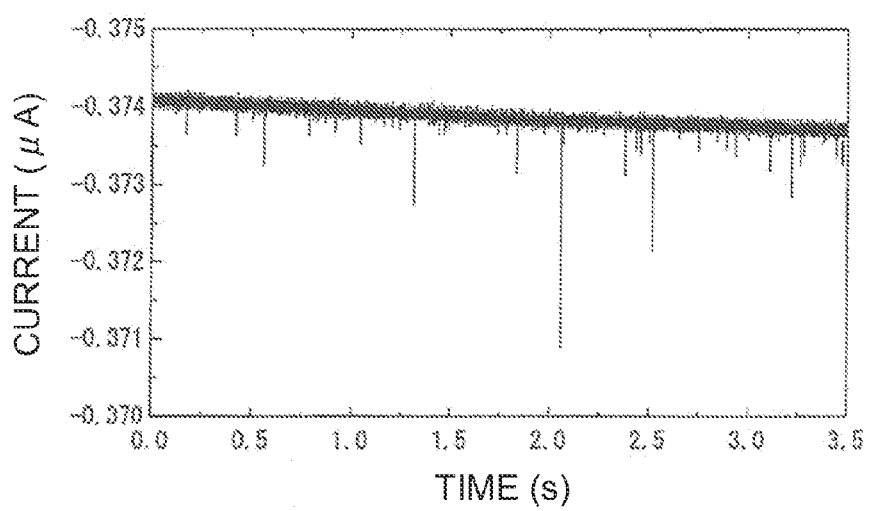
FIG. 12A is a diagram showing a change in current flowing between a first electrode pair when various biological samples are employed in an example.
Figure 12B:
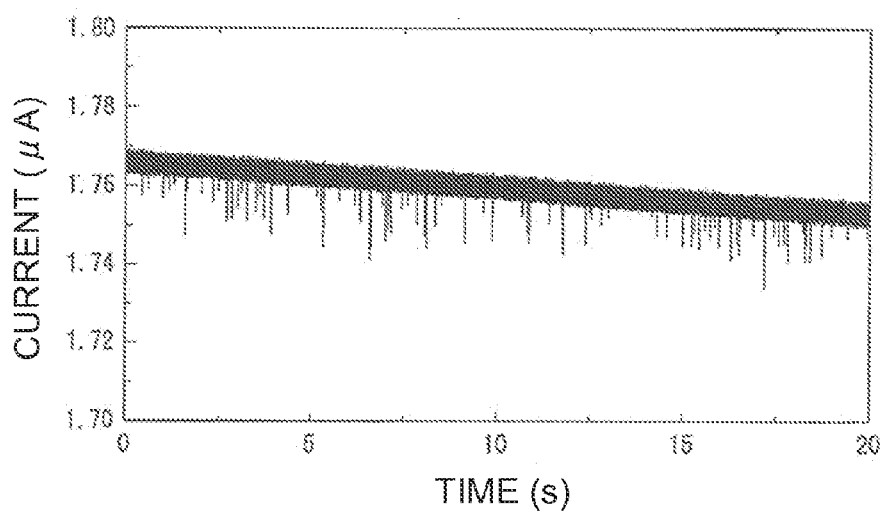
FIG. 12B is a diagram showing a change in current flowing between a first electrode pair when various biological samples are employed in an example.
Figure 12C:
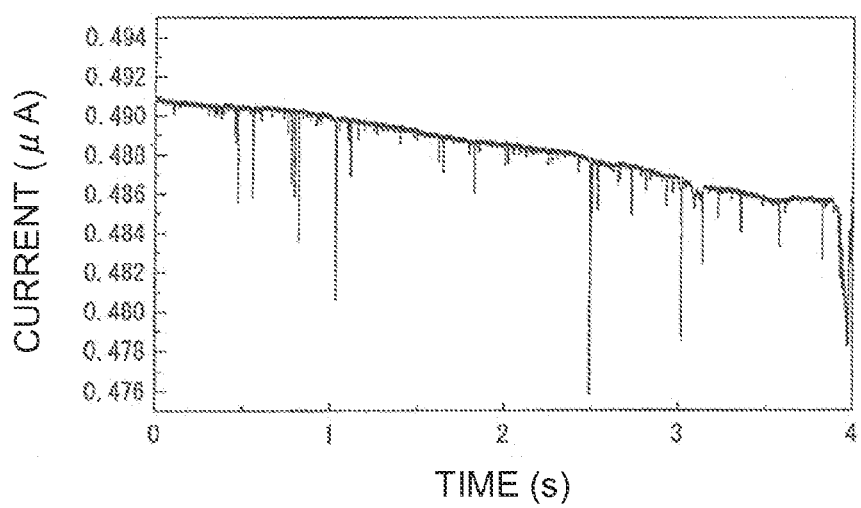
FIG. 12C is a diagram showing a change in current flowing between a first electrode pair when various biological samples are employed in an example.
Figure 13A:
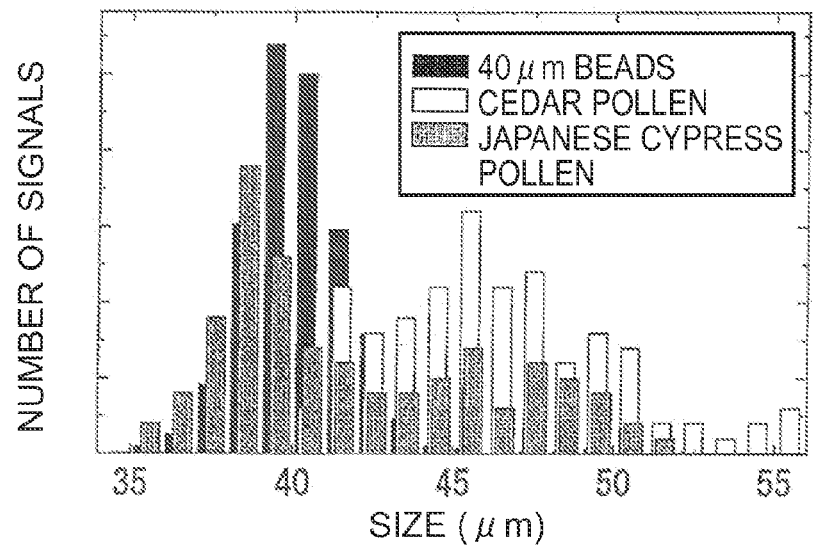
FIG. 13A is a diagram showing a change in current flowing between a first electrode pair when various biological samples are employed in an example.
Figure 13B:
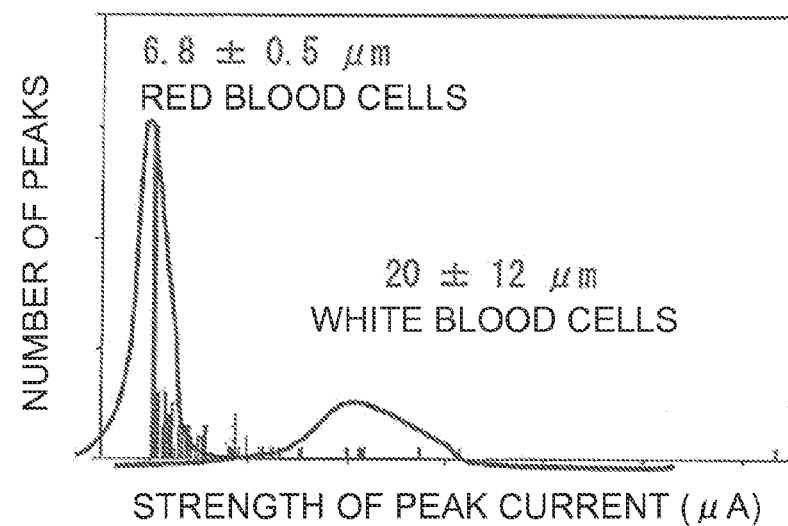
FIG. 13B is a diagram showing a change in current flowing between a first electrode pair when various biological samples are employed in an example.
Figure 13C:
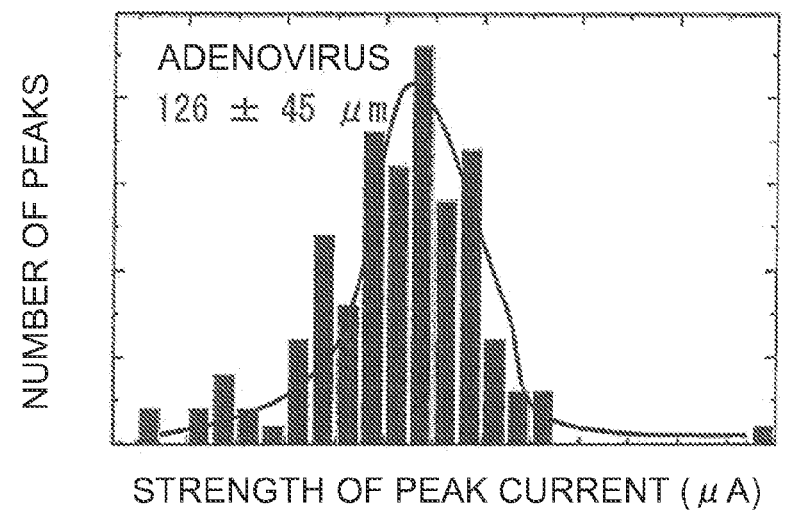
FIG. 13C is a diagram showing a change in current flowing between a first electrode pair when various biological samples are employed in an example.

As illustrated in FIG. 12A to FIG. 12C and in FIG. 13A to FIG. 13C, the value of the current flowing between the first electrode pair changes according to the size of the sample.

For example, when a device having a hole of 200 nm was employed, peaks of 2.3 μA (current value diminished by 0.32%) were the most numerous peak for Japanese cypress pollen, and peaks of 2.6 μA (current value diminished by 0.36%) were the most numerous peak for Japanese cedar pollen.

For example, when a device having a hole of 50 μm was employed, peaks of 0.15 nA (current value diminished by 0.15%) were the most numerous peak for red blood cells, and peaks of 2.6 nA (current value diminished by 0.7%) were the most numerous peak for white blood cells.

For example, when a device having a hole of 200 nm was employed, peaks of 8 nA (current value diminished by 0.8%) were the most numerous peak for adenovirus.

INDUSTRIAL APPLICABILITY

The invention enables utilization of various devices for analysis of various samples. For example, utilization can be made in devices that perform virus tests or allergen tests with high speed, high sensitivity, and at low cost.

The invention claimed is:

1. A sample analysis method, comprising:
  (a) applying a voltage between a first electrode pair, which is formed so as to sandwich a migration pathway of a sample such that an electric field is formed in a direction intersecting a migration direction of the sample;
  (b) causing a first current, which arises from a redox reaction, to flow to the first electrode pair by placing, within the migration pathway interposed between the first electrode pair, a solution including an electrochemically active molecule that produces the redox reaction at the first electrode pair;
  (c) causing the sample to migrate along the migration pathway interposed between the first electrode pair; and
  (d) measuring an amount of change in the first current produced by migration of the sample.

2. The sample analysis method according to claim 1, further comprising calculating a volume of the sample from the measured amount of change in the first current, based on a correlation between a known volume of a reference sample and an amount of change in the first current, or an amount of change in a physical quantity according to the first current for the reference sample.

3. The sample analysis method according to claim 1, further comprising calculating a quantity of charge of the sample from the measured amount of change in the first current, based on a correlation between a known charge quantity of a reference sample and an amount of change in the first current, or an amount of change in a physical quantity according to the first current for the reference sample.

4. The sample analysis method according to claim 1, wherein:
  (a) further comprises applying a voltage between a second electrode pair, which is formed so as to sandwich the migration pathway of the sample such that an electric field is formed in a direction substantially parallel to the migration direction of the sample;

(b) further comprises causing a second current to flow to the second electrode pair, wherein said second current arises from migration of ions contained in the solution along the migration direction of the sample through the migration pathway interposed between the first electrode pair; and (d) further comprises measuring an amount of change in the second current produced by the migration of the sample.

5. The sample analysis method according to claim 4, further comprising calculating a volume of the sample from the measured amount of change in the second current, based on a correlation between a known volume of a reference sample and an amount of change in the second current, or an amount of change in a physical quantity according to the second current for the reference sample.

6. The sample analysis method according to claim 4, wherein:
the first electrode pair comprises gold electrodes or platinum electrodes;
the second electrode pair comprises silver/silver chloride electrodes; and
the ions comprise chloride ions.

7. The sample analysis method according to claim 6, wherein the chloride ions have a concentration of from about 1 mM to about 1 M.

8. The sample analysis method according to claim 4, wherein a distance between an anode and a cathode of the second electrode pair is less than about 100 micrometers.

9. The sample analysis method according to claim 1, wherein the electrochemically active molecule comprises a metal complex, an organometallic complex, or an organic molecule.

10. The sample analysis method according to claim 9, wherein the electrochemically active molecule comprises a potassium hexacyanoferrate complex, a hexamine ruthenium complex chloride, or hydroxyferrocene.

11. The sample analysis method according to claim 9, wherein the electrochemically active molecule causes a redox reaction when a voltage of −1V to 1V is applied.

12. The sample analysis method according to claim 1, wherein a distance between an anode and a cathode of the first electrode pair is at least 2 nm.

13. The sample analysis method according to claim 1, wherein the direction of the electric field and the migration direction of the sample intersect at an angle of from about 45° to about 90°.

14. The sample analysis method according to claim 1, wherein the sample is spherical, and wherein a distance between an anode and a cathode of the first electrode pair is less than about 100 times a diameter of the sample.

15. The sample analysis method according to claim 1, wherein the sample comprises nucleic acids or amino acids.

* * * * *